United States Patent
Patel et al.

(10) Patent No.: US 10,357,277 B2
(45) Date of Patent: Jul. 23, 2019

(54) HIGH SPEED CHRONIC TOTAL OCCLUSION CROSSING DEVICES

(71) Applicant: AVINGER, INC., Redwood City, CA (US)

(72) Inventors: Himanshu N. Patel, San Jose, CA (US); John B. Simpson, Woodside, CA (US); Ryan Radjabi, Campbell, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

(21) Appl. No.: 15/324,325

(22) PCT Filed: Jul. 8, 2015

(86) PCT No.: PCT/US2015/039585
§ 371 (c)(1),
(2) Date: Jan. 6, 2017

(87) PCT Pub. No.: WO2016/007652
PCT Pub. Date: Jan. 14, 2016

(65) Prior Publication Data
US 2018/0146978 A1    May 31, 2018

Related U.S. Application Data

(60) Provisional application No. 62/022,101, filed on Jul. 8, 2014, provisional application No. 62/073,850, filed on Oct. 31, 2014.

(51) Int. Cl.
*A61B 17/32* (2006.01)
*A61B 17/3207* (2006.01)
(Continued)

(52) U.S. Cl.
CPC .. *A61B 17/320758* (2013.01); *A61B 1/00165* (2013.01); *A61B 1/3137* (2013.01);
(Continued)

(58) Field of Classification Search
CPC ...... A61B 17/320758; A61B 17/00234; A61B 1/3137; A61B 1/00165; A61B 2090/3983; A61B 2090/3614
(Continued)

(56) References Cited

U.S. PATENT DOCUMENTS 3,908,637 A    9/1975    Doroshow
4,178,935 A    12/1979    Gekhaman et al.
(Continued)

FOREIGN PATENT DOCUMENTS

CN    1875242 A    12/2006
CN    1947652 A    4/2007
(Continued)

OTHER PUBLICATIONS

Shinkle et al.; Evaluation of stent placement and outcomes with optical coherence tomography; Interv. Cardiol.; 2(4); pp. 535-543; (manuscript version, 12 pages); Aug. 2010.
(Continued)

*Primary Examiner* — Katherine M Shi
*Assistant Examiner* — Andrew P. Restaino
(74) *Attorney, Agent, or Firm* — Shay Glenn LLP

(57) ABSTRACT

An occlusion crossing device includes an outer shaft, an inner shaft, an optical fiber, and a handle attached to the inner shaft and the outer shaft. The inner shaft extends within the outer shaft. The inner shaft includes a drill tip at a distal end thereof. The optical fiber extends within the inner shaft substantially along a central axis of the inner shaft. The distal tip of the optical fiber is attached to the drill tip. The handle is configured to rotate the inner shaft and drill tip at speeds of greater than 500 rpm.

31 Claims, 21 Drawing Sheets

(51) Int. Cl.
*A61B 1/00* (2006.01)
*A61B 1/313* (2006.01)
*A61B 17/00* (2006.01)
*A61B 17/22* (2006.01)
*A61B 90/00* (2016.01)

(52) U.S. Cl.
CPC .............. *A61B 17/00234* (2013.01); *A61B 2017/00309* (2013.01); *A61B 2017/00455* (2013.01); *A61B 2017/00907* (2013.01); *A61B 2017/22094* (2013.01); *A61B 2017/320775* (2013.01); *A61B 2090/3614* (2016.02); *A61B 2090/3735* (2016.02); *A61B 2090/3983* (2016.02)

(58) Field of Classification Search
USPC ......................................................... 606/159
See application file for complete search history.

(56) References Cited

U.S. PATENT DOCUMENTS

| | | |
|---|---|---|
| 4,487,206 A | 12/1984 | Aagard |
| 4,527,553 A | 7/1985 | Upsher |
| 4,552,554 A | 11/1985 | Gould et al. |
| 4,621,353 A | 11/1986 | Hazel et al. |
| 4,639,091 A | 1/1987 | Huignard et al. |
| 4,654,024 A | 3/1987 | Crittenden et al. |
| 4,686,982 A | 8/1987 | Nash |
| 4,691,708 A | 9/1987 | Kane |
| 4,771,774 A | 9/1988 | Simpson et al. |
| 4,841,977 A | 6/1989 | Griffith et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,258,023 A | 11/1993 | Reger |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,383,460 A | 1/1995 | Jang et al. |
| 5,383,467 A | 1/1995 | Auer et al. |
| 5,425,273 A | 6/1995 | Chevalier |
| 5,429,136 A | 7/1995 | Milo et al. |
| 5,431,673 A | 7/1995 | Summers et al. |
| 5,437,284 A | 8/1995 | Trimble |
| 5,459,570 A | 10/1995 | Swanson et al. |
| 5,460,168 A | 10/1995 | Masubuchi et al. |
| 5,465,147 A | 11/1995 | Swanson |
| 5,507,795 A | 4/1996 | Chiang et al. |
| 5,556,405 A | 9/1996 | Lary |
| 5,607,394 A | 3/1997 | Andersen et al. |
| 5,620,426 A | 4/1997 | Braithwaite |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,984,973 A | 11/1999 | Girard et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,546,272 B1 * | 4/2003 | MacKinnon ....... A61B 1/00183 600/407 |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,615,071 B1 | 9/2003 | Casscells, III et al. |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |

(56) References Cited

U.S. PATENT DOCUMENTS

| | | |
|---|---|---|
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,893,460 B2 | 5/2005 | Spenser et al. |
| 6,936,067 B2 | 8/2005 | Buchanan |
| 6,945,997 B2 | 9/2005 | Huynh et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,261,732 B2 | 8/2007 | Justino |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,402,171 B2 | 7/2008 | Osborne et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,455,689 B2 | 11/2008 | Johnson |
| 7,474,407 B2 | 1/2009 | Gutin |
| 7,485,127 B2 | 2/2009 | Nistal |
| 7,488,340 B2 | 2/2009 | Kauphusman et al. |
| 7,510,575 B2 | 3/2009 | Spenser et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,803,186 B1 | 9/2010 | Li et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,846,203 B2 | 12/2010 | Cribier |
| 7,944,568 B2 | 5/2011 | Teramura et al. |
| 7,952,718 B2 | 5/2011 | Li et al. |
| 7,972,299 B2 | 7/2011 | Carter et al. |
| 8,057,540 B2 | 11/2011 | Letac et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,317,858 B2 | 11/2012 | Straubinger et al. |
| 8,323,336 B2 | 12/2012 | Hill et al. |
| 8,361,097 B2 | 1/2013 | Patel et al. |
| 8,403,983 B2 | 3/2013 | Quadri et al. |
| 8,425,593 B2 | 4/2013 | Braido et al. |
| 8,548,571 B2 | 10/2013 | He et al. |
| 8,548,603 B2* | 10/2013 | Swoyer .............. A61N 1/0551 600/101 |
| 8,562,672 B2 | 10/2013 | Bonhoeffer et al. |
| 8,568,475 B2 | 10/2013 | Nguyen et al. |
| 8,628,566 B2 | 1/2014 | Eberhardt et al. |
| 8,632,557 B2 | 1/2014 | Thatcher et al. |
| 8,644,913 B2 | 2/2014 | Simpson et al. |
| 8,673,000 B2 | 3/2014 | Tabor et al. |
| 8,696,695 B2* | 4/2014 | Patel .............. A61B 17/320758 606/159 |
| 8,709,077 B2 | 4/2014 | Schreck |
| 8,801,779 B2 | 8/2014 | Seguin et al. |
| 8,906,083 B2 | 12/2014 | Obermiller et al. |
| 8,911,459 B2 | 12/2014 | Simpson et al. |
| 8,956,404 B2 | 2/2015 | Börtlein et al. |
| 8,986,373 B2 | 3/2015 | Chau et al. |
| 8,998,976 B2 | 4/2015 | Gregg et al. |
| 9,011,521 B2 | 4/2015 | Haug et al. |
| 9,011,527 B2 | 4/2015 | Li et al. |
| 9,060,857 B2 | 6/2015 | Nguyen et al. |
| 9,101,467 B2 | 8/2015 | Eberhardt et al. |
| 9,119,662 B2 | 9/2015 | Moberg |
| 9,125,562 B2 | 9/2015 | Spencer et al. |
| 9,132,009 B2 | 9/2015 | Hacohen et al. |
| 9,155,617 B2 | 10/2015 | Carpentier et al. |
| 9,168,130 B2 | 10/2015 | Straubinger et al. |
| 9,168,131 B2 | 10/2015 | Yohanan et al. |
| 9,232,994 B2 | 1/2016 | Miller |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,351,757 B2 | 5/2016 | Kusleika |
| 9,387,071 B2 | 7/2016 | Tuval et al. |
| 9,393,110 B2 | 7/2016 | Levi et al. |
| 9,414,913 B2 | 8/2016 | Beith et al. |
| 9,421,083 B2 | 8/2016 | Eidenschink et al. |
| 9,474,605 B2 | 10/2016 | Rowe et al. |
| 9,474,609 B2 | 10/2016 | Haverkost et al. |
| 9,480,556 B2 | 11/2016 | Revuelta et al. |
| 9,480,558 B2 | 11/2016 | Destefano |
| 9,480,559 B2 | 11/2016 | Vidlund et al. |
| 9,480,563 B2 | 11/2016 | Li |
| 9,486,306 B2 | 11/2016 | Tegels et al. |
| 9,498,247 B2 | 11/2016 | Patel et al. |
| 9,498,330 B2 | 11/2016 | Solem |
| 9,498,600 B2 | 11/2016 | Rosenthal et al. |
| 9,504,564 B2 | 11/2016 | Nguyen et al. |
| 9,504,568 B2 | 11/2016 | Ryan et al. |
| 9,510,943 B2 | 12/2016 | Mesana et al. |
| 9,557,156 B2 | 1/2017 | Kankaria |
| 9,572,492 B2 | 2/2017 | Simpson et al. |
| 9,592,075 B2 | 3/2017 | Simpson et al. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |

(56) References Cited

U.S. PATENT DOCUMENTS

| | | |
|---|---|---|
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0181855 A1* | 9/2003 | Simpson ............ A61M 25/0041 604/95.04 |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1* | 12/2004 | Manning .............. A61B 5/0422 604/95.04 |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0096738 A1 | 5/2005 | Cali et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0078469 A1 | 4/2007 | Soito et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0049225 A1 | 2/2010 | To et al. |
| 2010/0080016 A1 | 4/2010 | Fukui et al. |
| 2010/0125253 A1 | 5/2010 | Olson |
| 2010/0130996 A1 | 5/2010 | Doud et al. |

(56) References Cited

U.S. PATENT DOCUMENTS

| | | |
|---|---|---|
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0295363 A1 | 12/2011 | Girard et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0046679 A1* | 2/2012 | Patel .................. A61B 1/00179 606/159 |
| 2012/0123352 A1 | 5/2012 | Fruland et al. |
| 2012/0197391 A1 | 8/2012 | Alkhatib et al. |
| 2012/0238869 A1 | 9/2012 | Schmitt et al. |
| 2012/0259337 A1 | 10/2012 | del Rio et al. |
| 2012/0289971 A1 | 11/2012 | Segermark et al. |
| 2013/0035692 A1 | 2/2013 | Sorensen et al. |
| 2013/0096589 A1 | 4/2013 | Spencer et al. |
| 2013/0110143 A1* | 5/2013 | Noriega ......... A61B 17/320758 606/159 |
| 2013/0123615 A1* | 5/2013 | Spencer ............... A61B 5/0066 600/427 |
| 2013/0138128 A1 | 5/2013 | Patel et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0289392 A1 | 10/2013 | Patel et al. |
| 2013/0296695 A1 | 11/2013 | Spencer et al. |
| 2013/0317519 A1 | 11/2013 | Romo et al. |
| 2014/0005534 A1 | 1/2014 | He et al. |
| 2014/0005775 A1 | 1/2014 | Alkhatib et al. |
| 2014/0012374 A1 | 1/2014 | Rankin |
| 2014/0128893 A1 | 5/2014 | Guggenheimer et al. |
| 2014/0187949 A1 | 7/2014 | Zhao et al. |
| 2014/0222047 A1 | 8/2014 | Vreeman |
| 2014/0291985 A1 | 10/2014 | Cabrera et al. |
| 2014/0343410 A1 | 11/2014 | Graf et al. |
| 2014/0371718 A1 | 12/2014 | Alvarez et al. |
| 2015/0025310 A1 | 1/2015 | Everingham et al. |
| 2015/0141816 A1 | 5/2015 | Gupta et al. |
| 2015/0146211 A1 | 5/2015 | Bhagavatula et al. |
| 2015/0164530 A1 | 6/2015 | Carver et al. |
| 2015/0208922 A1 | 7/2015 | Simpson et al. |
| 2015/0272615 A1 | 10/2015 | Newhauser et al. |
| 2015/0320975 A1 | 11/2015 | Simpson et al. |
| 2016/0008025 A1 | 1/2016 | Gupta et al. |
| 2016/0029902 A1 | 2/2016 | Smith et al. |
| 2016/0038030 A1 | 2/2016 | Smith et al. |
| 2016/0135832 A1 | 5/2016 | Simpson et al. |
| 2016/0144155 A1 | 5/2016 | Simpson et al. |
| 2016/0262791 A1 | 9/2016 | Patel et al. |
| 2016/0262839 A1 | 9/2016 | Spencer et al. |
| 2016/0310269 A1 | 10/2016 | Braido |
| 2016/0338582 A1 | 11/2016 | Tachibana et al. |
| 2018/0256187 A1 | 9/2018 | Patel et al. |

FOREIGN PATENT DOCUMENTS

| | | |
|---|---|---|
| CN | 101601581 A | 12/2009 |
| CN | 103027727 A | 4/2013 |
| DE | 202006018883.5 U | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |
| JP | S62-275425 A | 11/1987 |
| JP | 03502060 A | 2/1990 |
| JP | 05103763 A | 4/1993 |
| JP | 06027343 A | 2/1994 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2010042182 A | 2/2010 |
| JP | 2010518900 A | 6/2010 |
| JP | 2011521747 A | 7/2011 |
| JP | 2012533353 A | 12/2012 |
| JP | 2016508758 A | 3/2016 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/061935 A1 | 5/2012 |
| WO | WO2012/166332 A1 | 12/2012 |
| WO | WO2013/033490 A1 | 3/2013 |

(56) References Cited

FOREIGN PATENT DOCUMENTS

| WO | WO2013/056262 A1 | 4/2013 |
|---|---|---|
| WO | WO2015/074018 A1 | 5/2015 |
| WO | WO2015/120146 A1 | 8/2015 |
| WO | WO2017/007853 A1 | 1/2017 |

OTHER PUBLICATIONS

Kankaria; U.S. Appl. No. 15/419,815 entitled "Optical coherence tomography with graded index fiber for biological imaging," filed Jan. 30, 2017.
Simpson et al.; U.S. Appl. No. 15/434,758 entitled "Occlusion-crossing devices, imaging, and atherectomy devices," filed Feb. 16, 2017.
Simpson et al.; U.S. Appl. No. 15/457,960 entitled "Atherectomy catheters devices having multi-channel bushings," filed Mar. 13, 2017.
Patel et al.; U.S. Appl. No. 15/480,238 entitled "Guidewire positioning catheter," filed Apr. 5, 2017.
Smith et al.; U.S. Appl. No. 15/854,579 entitled "Chronic total occusion crossing devices with imaging," filed Dec. 26, 2017.
Patel et al.; U.S. Appl. No. 15/741,928 entitled "Micro-molded anamorpjic reflector lens for image guided therapeutic/diagnostic catheters," filed Jan. 4, 2018.
Zung et al.; U.S. Appl. No. 15/741,773 entitled "Self-alignment mechanism for imaging cather and drive assembly," filed Jan. 4, 2018.
Aziz et al.; Chronic total occlusions—a stiff challege requiring a major breakthrough: is there light at the end of the tunnel?; Heart; vol. 91; suppl. III; pp. 42-48; Jun. 2005.
Emkey et al.; Analysis and evaluation of graded-index fiber-lenses; Journal of Lightwave Technology; vol. LT-5; No. 9; pp. 1156-1164; Sep. 1987.
Gonzalo et al.; Optical coherence tomography patterns of stent restenosis; Am. Heart J.; 158(2); pp. 284-293; Aug. 2009.
Linares et al.; Arbitrary single-mode coupling by tapered and nontapered grin fiber lenses; Applied Optics; vol. 29; No. 28; pp. 4003-4007; Oct. 1, 1990.
Sharma et al.; Optical coherence tomography based on an all-fiber autocorrelator using probe-end reflection as reference; CWJ13; San Francisco, California; CLEO May 16, 2004; 4 pages.
Suparno et al.; Light scattering with single-mode fiber collimators; Applied Optics; vol. 33; No. 30; pp. 7200-7205; Oct. 20, 1994.
Han et al.; In situ Frog Retina Imaging Using Common-Path OCT with a Gold-Coated Bare Fiber Probe; CFM6; San Jose, California; CLEO, May 4, 2008; 2 pages.
Muller et al.; Time-gated infrared fourier-domain optical coherence tomography; CFM5; San Jose, California; CLEO May 4, 2008; 2 pages.
Tanaka et al.; Challenges on the frontier of intracoronary imaging: atherosclerotic plaque macrophage measurement by optical coherence tomography; Journal of Biomedical Optics; 15(1); pp.(011104-1)-(011104-8); Jan.-Feb. 2010.
Wang et al.; Common-path endoscopic Fourier domain OCT with a reference Michelson interferometer; Proceedings of the SPIE; vol. 7566; pp. 75660L-75660L-7; Jan. 2010.
Rosenthal et al.; U.S. Appl. No. 15/354,898 entitled "Atherectomy catheter with laterally-displaceable tip," filed Nov. 17, 2017.
Patel et al.; U.S. Appl. No. 15/354,842 entitled "Atherectomy catheters and occlusion crossing devices," filed Nov. 17, 2016.
Black et al.; U.S. Appl. No. 15/783,800 entitled "Optical coherence tomography for biological imaging," filed Oct. 13, 2017.
Newhauser et al.; U.S. Appl. No. 15/954,407 entitled "Occlusion-crossing devices," filed Apr. 16, 2018.
Christensen; U.S. Appl. No. 16/069,545 entitled "OCT imaging catheter with lag correction," filed Jul. 12, 2018.
Rosenthal et al.; U.S. Appl. No. 16/105,743 entitled "Atherectomy catheter with laterally-displaceable tip," filed Aug. 20, 2018.

\* cited by examiner

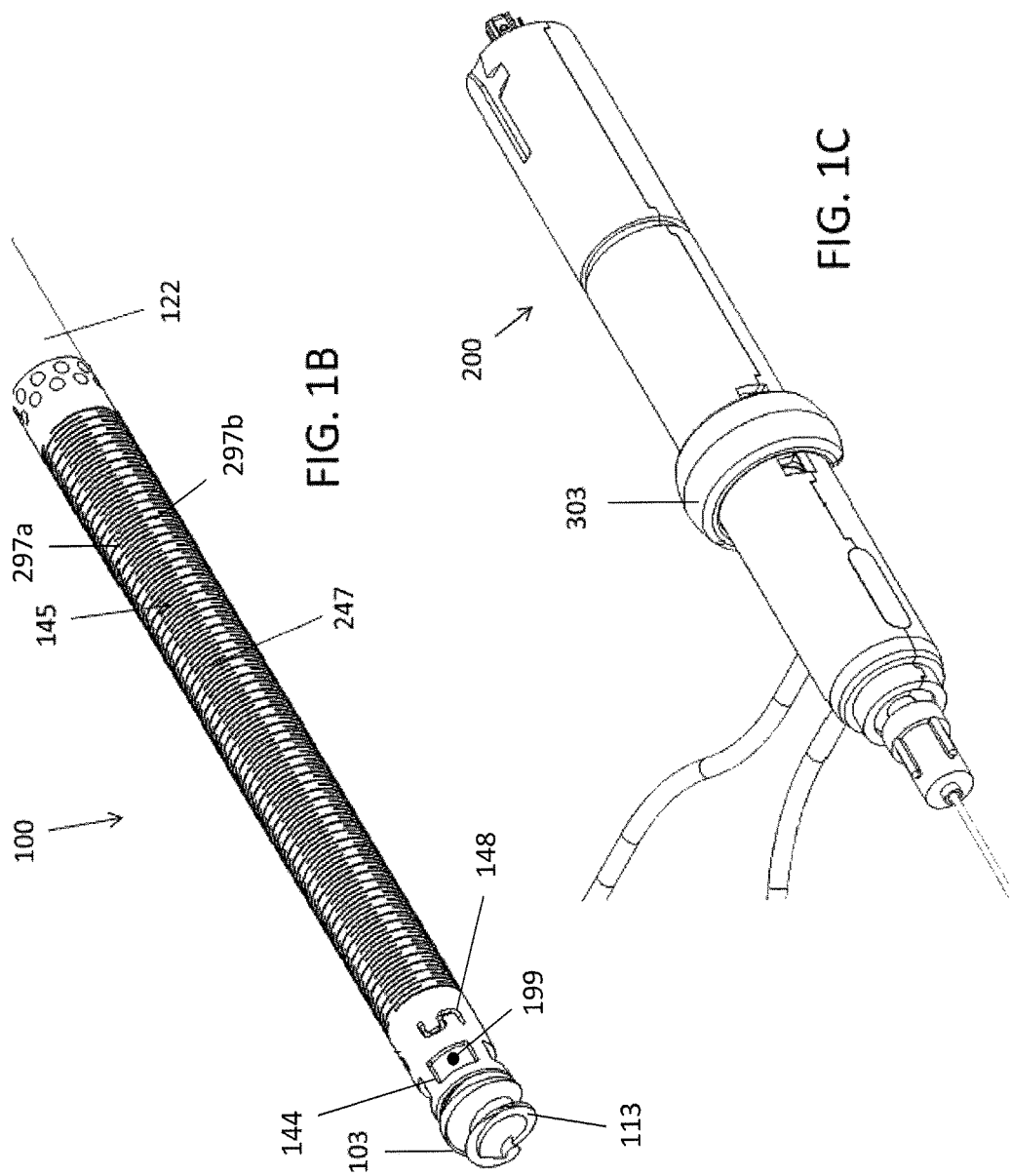

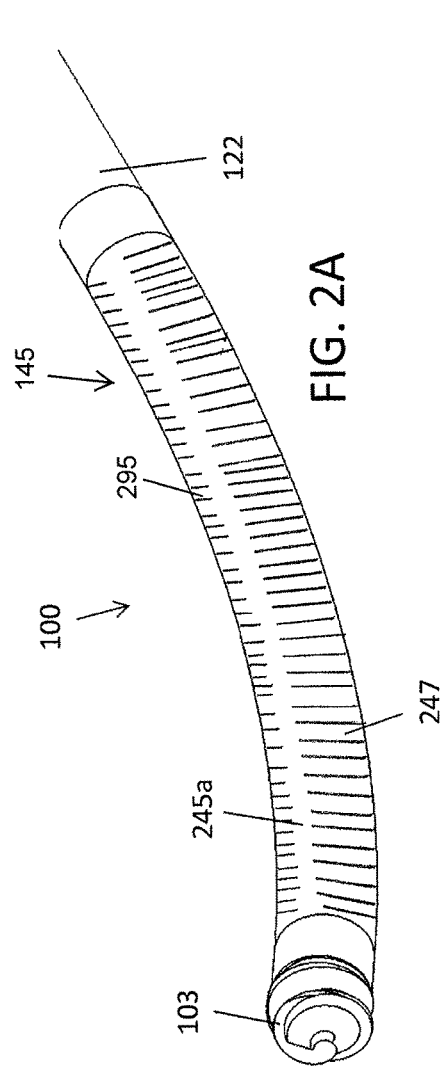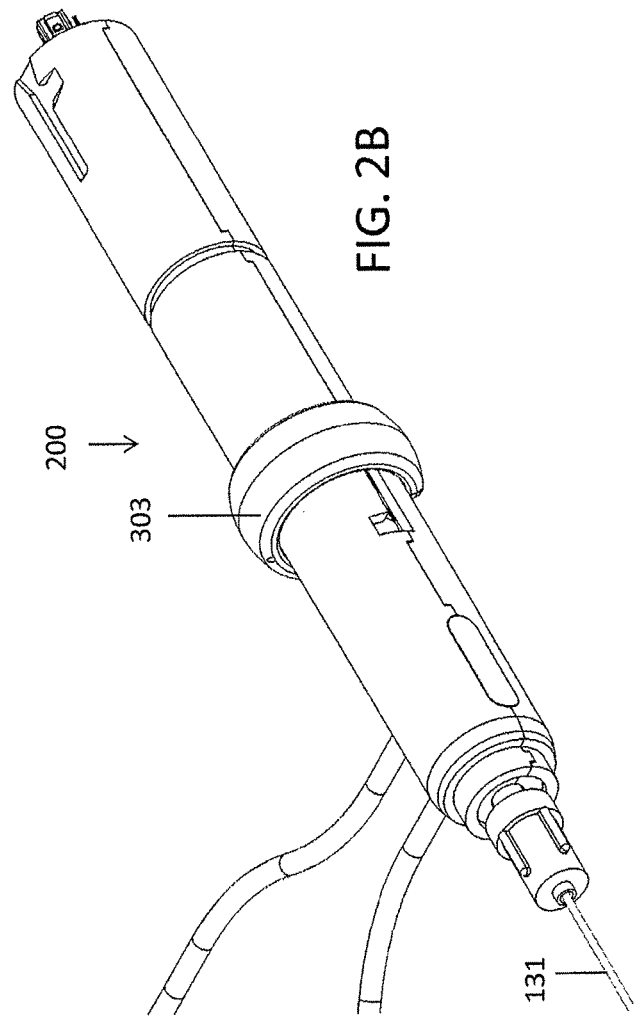

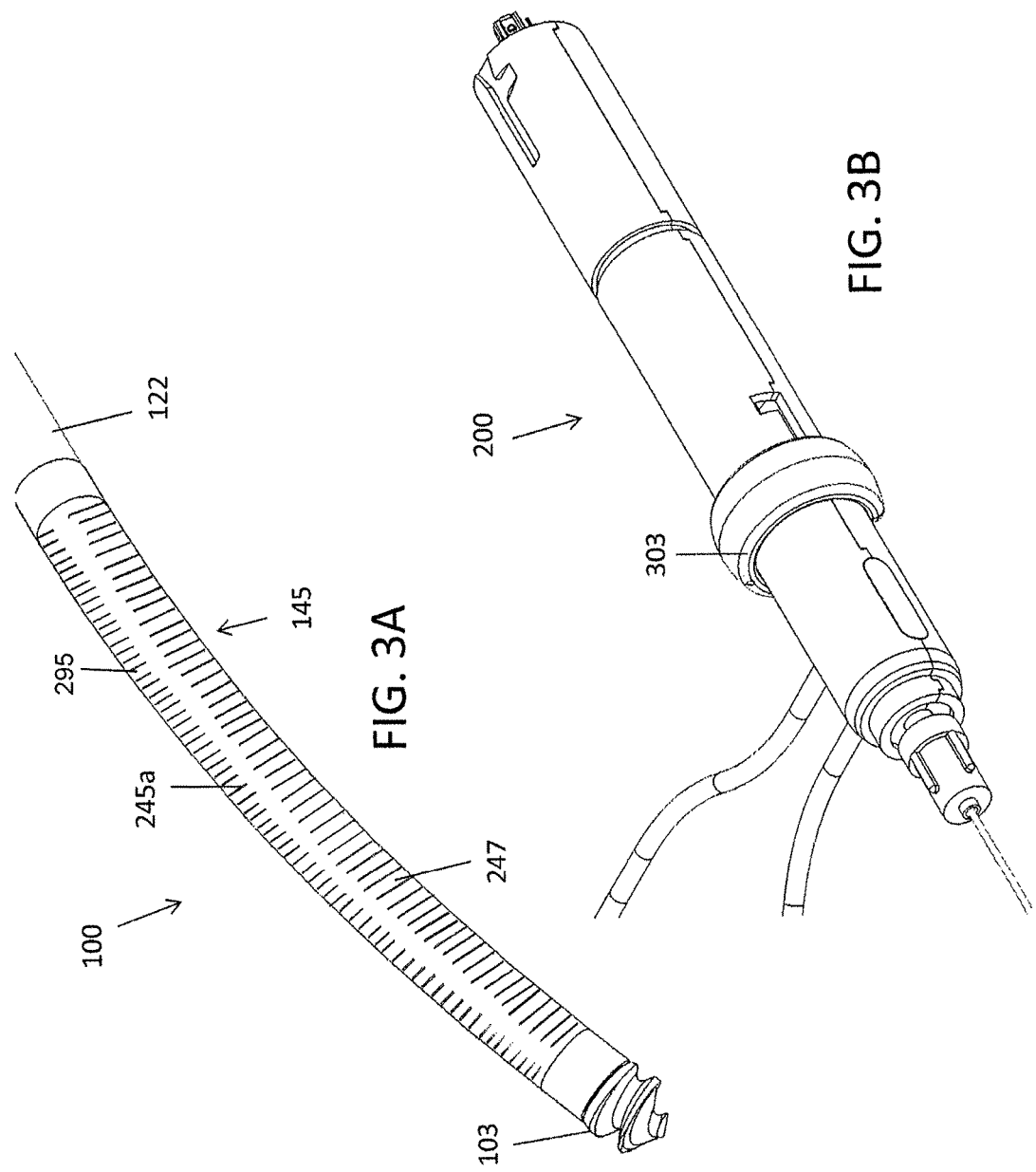

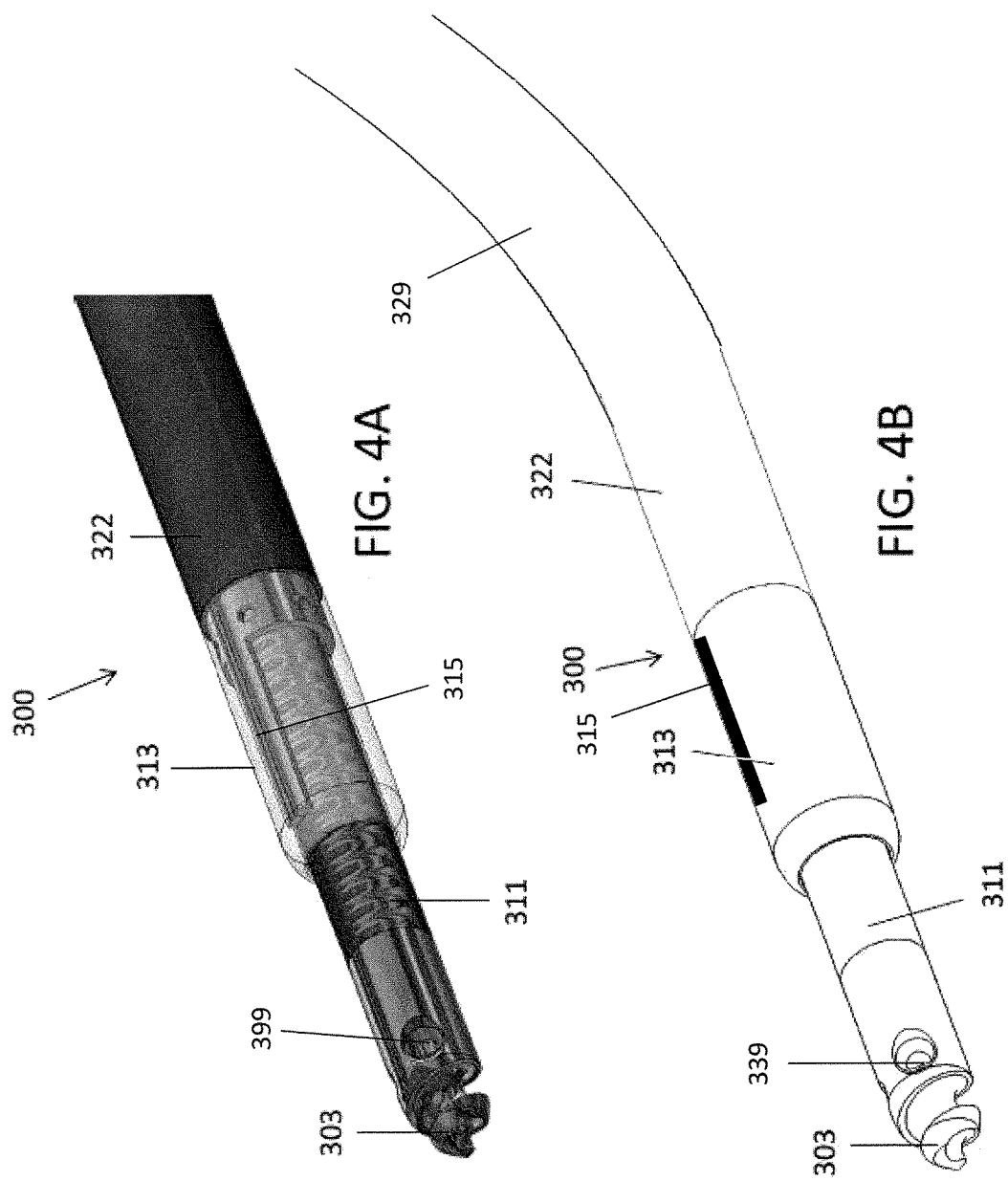

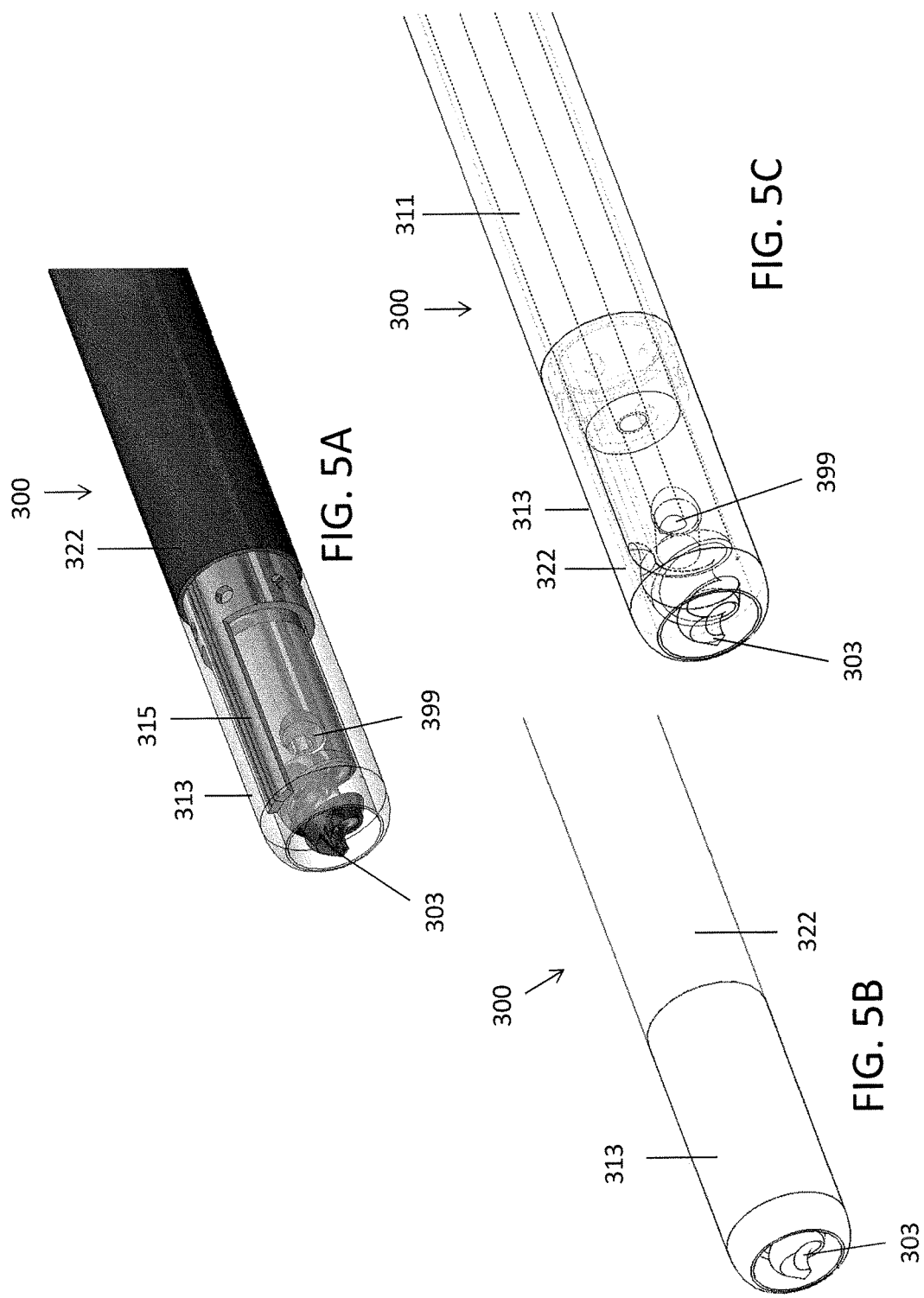

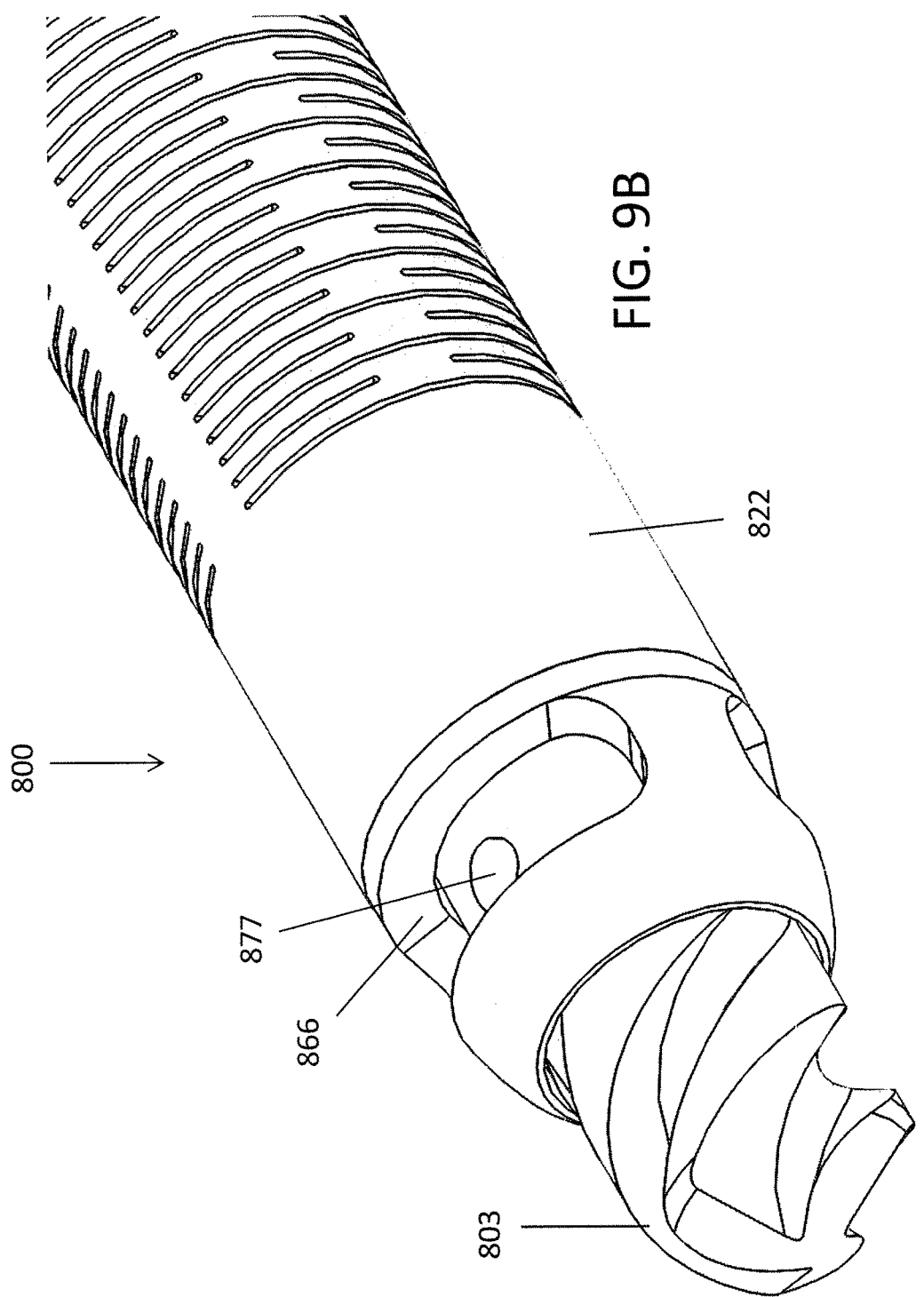

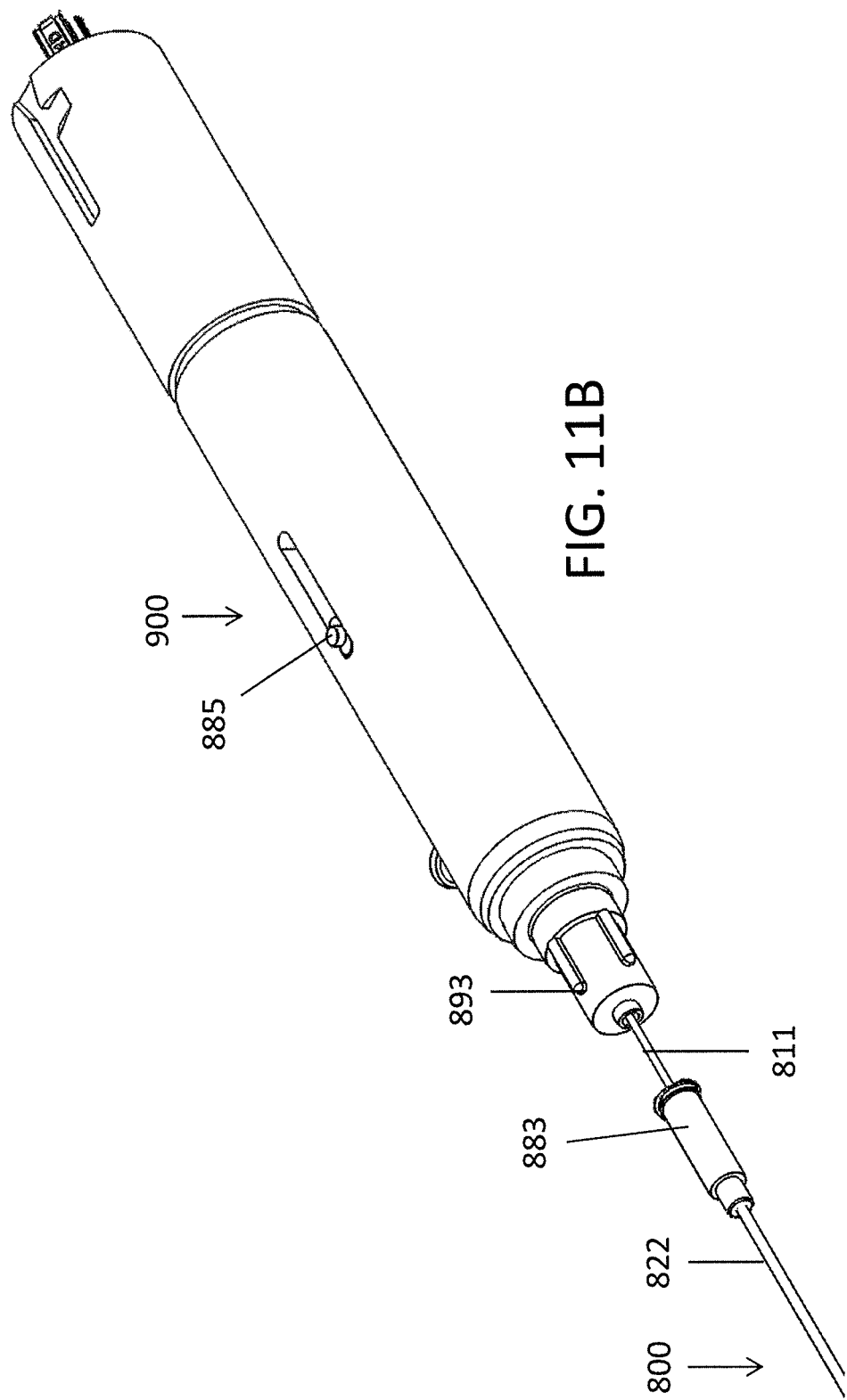

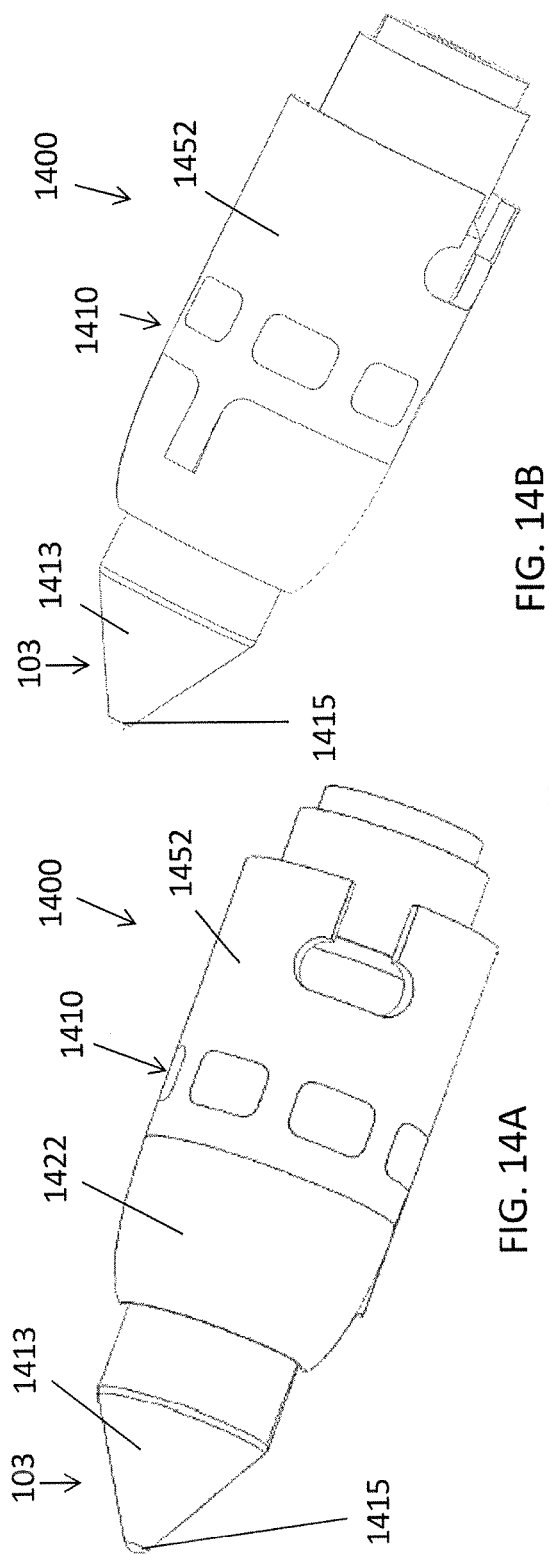
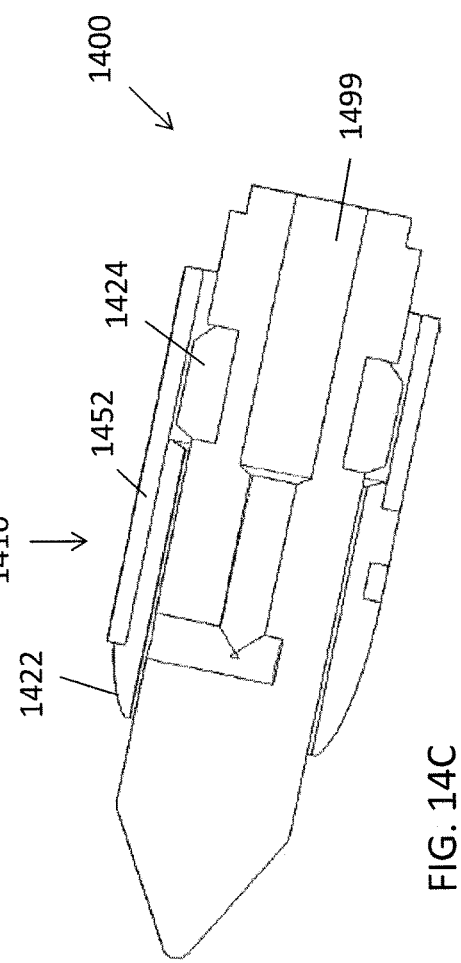
FIG. 14A
FIG. 14B
FIG. 14C

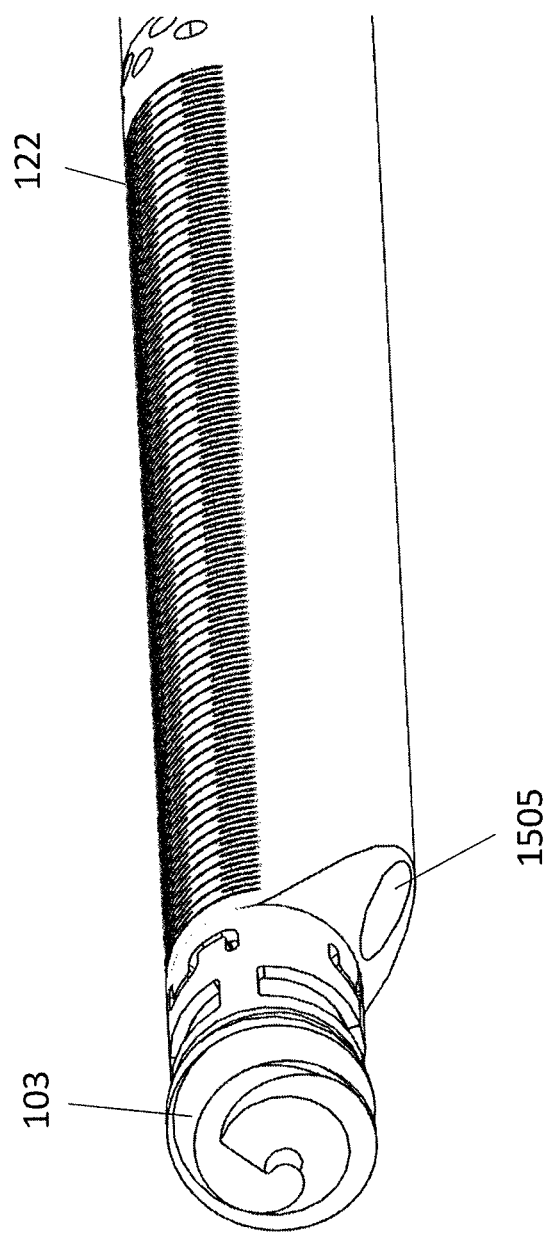

HIGH SPEED CHRONIC TOTAL OCCLUSION CROSSING DEVICES

CROSS REFERENCE TO RELATED APPLICATIONS

This application claims priority to U.S. Provisional Application No. 62/022,101, titled "HIGH SPEED CHRONIC TOTAL OCCLUSION CROSSING DEVICES," and filed Jul. 8, 2014, the entire contents of which are incorporated by reference herein. This application also claims priority to U.S. Provisional Application No. 62/073,850, titled "HIGH SPEED CHRONIC TOTAL OCCLUSION CROSSING DEVICES," and filed Oct. 31, 2014, the entire contents of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Peripheral artery disease (PAD) and coronary artery disease (CAD) affect millions of people in the United States alone. PAD and CAD are silent, dangerous diseases that can have catastrophic consequences when left untreated. CAD is the leading cause of death for in the United States while PAD is the leading cause of amputation in patients over 50 and is responsible for approximately 160,000 amputations in the United States each year.

Coronary artery disease (CAD) and Peripheral artery disease (PAD) are both caused by the progressive narrowing of the blood vessels most often caused by atherosclerosis, the collection of plaque or a fatty substance along the inner lining of the artery wall. Over time, this substance hardens and thickens, which may interfere with blood circulation to the arms, legs, stomach and kidneys. This narrowing forms an occlusion, completely or partially restricting flow through the artery. Blood circulation to the brain and heart may be reduced, increasing the risk for stroke and heart disease.

Interventional treatments for CAD and PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Other treatments may include angioplasty to open the artery. For example, a balloon angioplasty typically involves insertion of a catheter into a leg or arm artery and positioning the catheter such that the balloon resides within the blockage. The balloon, connected to the catheter, is expanded to open the artery. Surgeons may then place a wire mesh tube, called a stent, at the area of blockage to keep the artery open.

Such minimally invasive techniques (e.g., atherectomy, angioplasty, etc.) typically involve the placement of a guidewire through the occlusion. Using the guidewire, one or more interventional devices may be positioned to remove or displace the occlusion. Unfortunately, placement of the guidewire, while critical for effective treatment, may be difficult. In particular, when placing a guidewire across an occlusion, it may be difficult to pass the guidewire through the occlusion while avoiding damage to the artery. For example, it is often difficult to prevent the guidewire from directing out of the lumen into the adventitia and surrounding tissues, potentially damaging the vessel and preventing effective treatment of the occlusion.

As a result, occlusion-crossing devices, intended to assist in the passing of the guidewire through the occlusion, have been developed. Many of the devices, however, are ill equipped to be used with imaging, thereby making placement of the guidewire cumbersome and difficult. Moreover, many of the occlusion-crossing devices are too large to be used in small-diameter peripheral arteries or in coronary arteries.

Accordingly, occlusion crossing catheter devices designed to address some of these concerns are described herein.

SUMMARY OF THE DISCLOSURE

Described herein are occlusion-crossing devices having a low profile and a distal drill tip. In some embodiments, an articulating feature can provide for steering or directionality of the device. In some embodiments, an inner shaft can be removable from an outer shaft.

In general, in one embodiment, an occlusion crossing device includes an outer shaft, an inner shaft, an optical fiber, and a handle attached to the inner shaft and the outer shaft. The inner shaft extends within the outer shaft. The inner shaft includes a drill tip at a distal end thereof. The optical fiber extends within the inner shaft substantially along a central axis of the inner shaft. The distal tip of the optical fiber is attached to the drill tip. The handle is configured to rotate the inner shaft and drill tip at speeds of greater than 500 rpm.

This and other embodiments can include one or more of the following features. The inner shaft and optical fiber can be removable from the outer shaft. The handle can include a luer lock configured to lock and unlock the inner shaft relative to the outer shaft. The outer shaft can include an articulating feature configured to allow the outer shaft to bend. The articulating feature can be activated by moving the inner shaft along the central axis relative to the outer shaft. The articulating feature can include a backbone and a plurality of circumferential cuts. The inner shaft can include an annular member configured to engage with an inner lip of the outer shaft to bend the outer shaft when the inner shaft is pushed distally. The inner shaft can include an annular member configured to engage with an inner lip of the outer shaft to bend the outer shaft when the inner shaft is pulled proximally. The outer shaft can include a preformed bend therein. The outer shaft can further include a marker positioned with respect to the preformed bend such that an orientation of the outer shaft can be determined during imaging. The outer shaft can include a transparent distal portion configured to allow imaging with the optical fiber therethrough. The handle can be configured to rotate the inner shaft and drill tip at speeds of greater than 1,000 rpm. The handle can be configured to rate the inner shaft and drill tip at speeds of greater than 500 rpm such that images can be generated from the optical fiber at a rate of greater than or equal to 8 frames per second. The optical fiber can be a common path optical coherence tomography fiber. The drill tip can include a plurality of spiral cutting edges. The drill tip can be a substantially smooth frusto-conical tip. The imaging device can further include a monorail guidewire lumen extending along the outer shaft. An outer diameter of the outer shaft can be less than 0.08 inches.

In general, in one embodiment, a method of crossing an occlusion includes: (1) inserting a device into a vessel having an occlusion therein; (2) rotating an inner shaft of the device relative to an outer shaft of the device such that a drill tip on the inner shaft drills through the occlusion; and (3) generating images with an optical fiber extending through the inner shaft at a rate of greater than or equal to 8 frames per second while rotating the inner shaft.

This and other embodiments can include one or more of the following features. The method can further include removing the inner shaft from the outer shaft, and inserting a guidewire through the outer shaft. The method can further include bending a distal end of the device in order to steer the device through the vessel. Bending the distal end can comprise pushing or pulling on the inner shaft. The method can further include orienting a bend in the outer shaft in a desired direction. The method can further include using a marker on the device to orient the bend. Rotating the inner shaft can comprise rotating at more than 500 rpm.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-3B show an occlusion crossing device having an articulating feature.

FIGS. 4A-5C show an occlusion crossing device having separable inner and outer shafts.

FIGS. 9A and 9B show the inner shaft of the occlusion crossing device of FIGS. 8A-8B positioned inside of the outer shaft for cutting and imaging.

FIGS. 11A and 11B show an exemplary handle for use with the occlusion crossing device of FIGS. 8A-8B.

FIGS. 14A-14C show the distal portion of another embodiment of an occlusion crossing device.

FIG. 15 shows the occlusion crossing device FIGS. 1A-3B with a monorail guidewire lumen.

DETAILED DESCRIPTION

Figure 1A:
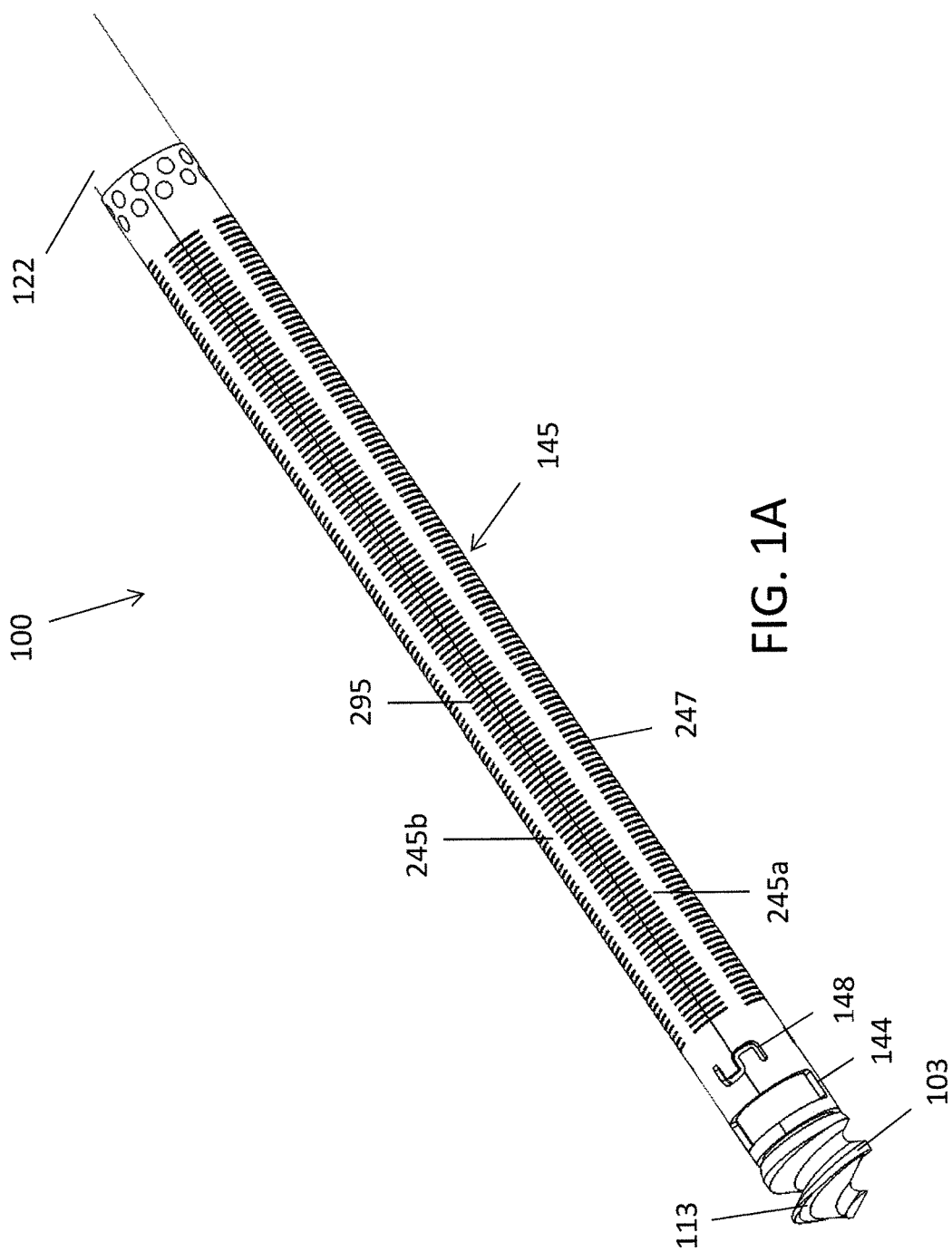
Figure 1D:
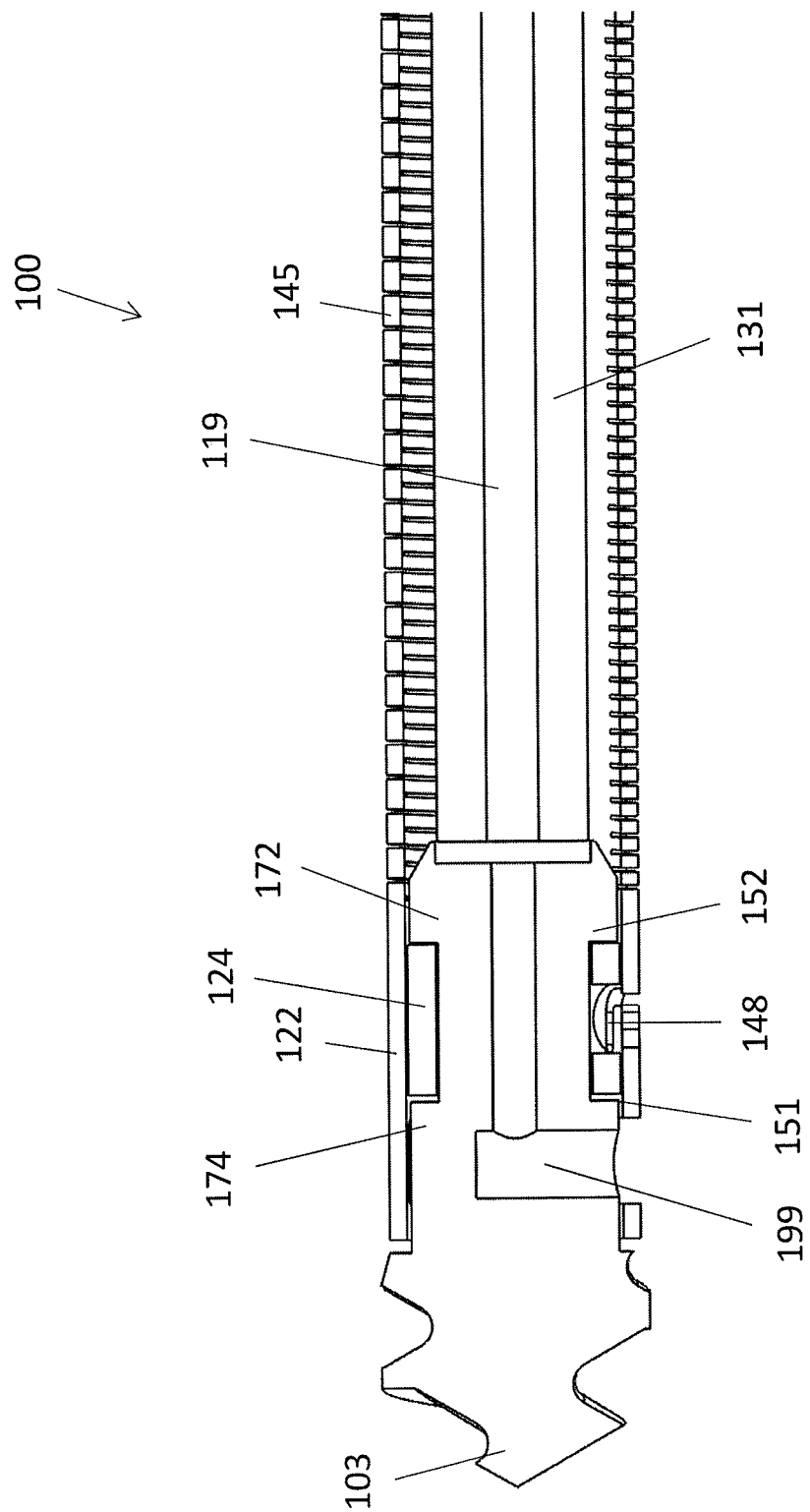

Described herein are occlusion-crossing devices having a low profile so as to be usable in small-diameter arteries and coronary arteries, e.g., through a 5 French catheter or smaller. In general, the devices described herein can have on-board imaging, such as optical coherence tomography (OCT) imaging. The optical fiber for OCT imaging can extend substantially along the central axis of the device, thereby decreasing the profile of the device and allowing for rotation at high speeds. The devices can also include a rotatable pointed tip, allowing for forward drilling. In some embodiments, the device can include an articulating distal end to enable steering of the device.

Referring to FIGS. 1A-3B, in one embodiment, an exemplary catheter 100 includes an outer shaft 122 and an inner driveshaft 131 connected to a distal tip 103. The elongate outer shaft 122 can be hollow and can have an inner diameter of approximately 1 mm and an outer diameter of approximately 1.5 mm. In some embodiments, the outer shaft 122 can have a coiled construction, whereby the coils are wound by laying one coil over another. For example, the shaft 122 can include at least two coil layers. Further, the coil layers can be counter-wound, such that one coil layer, such as the inner coil layer, has a left hand lay and another layer, such as the outer coil layer, has a right hand lay. The coil can provide torque in the direction that tightens the outer layer, cinching down on the inner layer. A third counter wound coil can be added to generate torque in both directions. In another embodiment, the shaft 122 is made of a braided wire reinforced polymeric shaft. In yet another embodiment, the shaft 122 can be a laser-cut tube. The outer shaft 122 can further include one or more imaging windows 144 at a distal end thereof.

A bushing 124 (see FIG. 1D) can be attached to the shaft 122, such as through a tab and slot mechanism 148. The bushing 124 can act as a bearing surface relative to the inner shaft or tip 103. Further, the bushing 124 can include edges or lips 151, 152 on either side configured to interact with the inner driveshaft 131 or the tip 103, as discussed further below.

The tip 103 can be configured, for example, to separate, dissect, or shred tissue. In some embodiments, the tip 103 can include sharp spiraling flutes 113 that come to a point in the center of the device. Further, the flutes 113 can be angled such that they have sharper edges when rotated in one direction than in another direction. As a result, the tip 103 with flutes 113 can have an active and passive modes depending upon the direction of rotation of the tip 103. In passive mode, the tip 103 with flutes 113 can be less aggressive, providing blunt dissection of tissue. In active mode, the tip 103 with flutes 113 can be more aggressive, providing cutting and auguring to make its way through harder material. In some embodiments, as described further below with respect to FIGS. 14A and 14B, the distal tip 103 can have a smooth angled surface that is non-fluted.

The inner driveshaft 131 (see FIG. 1D) can be connected to the distal tip 103 and can extend down the center of the outer shaft 122. The inner driveshaft 131 can be configured to rotate in either a single direction or in both the clockwise and counterclockwise directions so as to rotate the tip 103 relative to the shaft 122 (about the bushing 124) in either a single direction or in the clockwise or counterclockwise direction. Annular rings 174, 172 can be positioned around a distal portion of the inner driveshaft 131 and/or the tip 103. The rings 174, 172 can be positioned against the edges 151, 152 of the bushing 124. The annular bushing 124 can allow relative rotation of the inner driveshaft 131 relative to the bushing 124 while preventing axial movement (and allowing for articulation in some embodiments, as described further below).

In some embodiments, a distal portion of the outer shaft 122 can include an articulating feature 145. As shown in FIGS. 1A and 1B, the articulating feature 145 can include one or more backbones 245a, b and a series of circumferential cuts 247 and 295. The one or more backbones can be positioned on only one side of the catheter (e.g., span less than 180 degrees, less than 150 degrees, or less than 90 degrees). In some embodiments, and as shown in FIG. 1A, a series of small circumferential cuts 295 can extend between the two backbones 245a, b in order to provide added flexibility during bending. The circumferential cuts 247, 295 can be configured as incomplete rings or spirals about the outer shaft 122. Referring to FIG. 1B, in some embodiments, the circumferential cuts 247 can include one or more breaks 297a,b therein designed to provide additional tensile strength and compression resistance for the articulating feature 145.

The articulating feature 145 can be attached to the inner driveshaft 131 such that movement of the driveshaft 131 can activate the articulating feature. Further, in some embodiments, a handle 200 (see FIGS. 2B and 3B) can be used to activate movement of the driveshaft 131.

Referring to FIGS. 2A-2B, as the driveshaft 131 is pushed distally, the annular ring 172 can push distally on the proximal lip 152 of the bushing 124 (see FIG. 1D), causing the circumferential cuts 247 to spread apart or open while the backbones 245a,b maintain their length (and the circumferential cuts 295 move closer together). As a result, the articulating feature 145 can bend towards the backbones 245a,b. As shown in FIG. 2B, this bending mechanism can be activated on the handle 200, such as by moving a ring 303 distally and/or pushing or moving a button or lever.

Likewise, referring to FIGS. 3A-3B, as the driveshaft 131 is pulled proximally, the annular ring 174 can hit the distal lip 151 of the bushing 124. As further distal force is applied by the driveshaft 131, the circumferential cuts 247 can begin to move closer together and/or the material between the cuts 247 can overlap while the backbones 245a,b maintain their length (and the cuts 295 move further apart). As a result, the articulating feature 145 can bend towards the circumferential cuts 247 and away from the backbones 245a,b. As shown in FIG. 3B, this bending mechanism can be activated on the handle 200, such as by moving the ring 303 proximally and/or pushing or moving a button or lever.

The bending movement of the articulating feature 145 can advantageously allow the device 100 to be steered when used in the vessel, such as for re-entry if the tip extends out of the occlusion or lumen. In some embodiments, the catheter 100 can be configured to bend in only one direction by either pushing or pulling on the driveshaft 131 and return to the straight configuration shown in FIG. 1A by movement of the driveshaft 131 in the opposite direction.

The catheter 100 can further include an imaging element 199 attached to the driveshaft 131 and configured to rotate therewith. The imaging element 199 can be the distal end of an OCT fiber 119 extending down the center of the driveshaft 131. The imaging element 199 can provide imaging (through windows 144) as the catheter 100 is used in the vessel, thereby assisting in occlusion crossing.

Referring to FIG. 15, in some embodiments, a monorail guidewire lumen 1505 can extend along the outer shaft 122. The guidewire lumen 1505 can run, for example, between the two backbones 245a,b so as to not add additional stiffness to the flexible area with the circumferential cuts 247.

In some embodiments, the catheter 100 can be used with a sheath. The sheath can be hollow and include a hemostasis valve attached at the proximal end with a flush port on the side to facilitate flushing through the sheath. The sheath can also facilitate guidewire placement to the target site, particularly for embodiments of the catheter 100 that do not include a monorail guidewire lumen. That is, the catheter 100 can be used to cross the occlusion, the sheath can be placed thereover, the device removed, and then the guidewire can be introduced.

Referring to FIGS. 4A-5C, in another embodiment, an exemplary catheter 300 includes an inner shaft 311, an outer shaft 322, and a distal tip 303 connected to the inner shaft 311. Further, the outer shaft 322 can be separable from the inner shaft 311. For example, the inner shaft 311 can include a luer connector near the proximal end that is attachable and detachable from a luer connector on a proximal end of the outer shaft 322, as described below with respect to handle 900.

In some embodiments, a distal portion 313 of the outer shaft 322 can be clear or transparent, such as made of a clear or transparent plastic, in order to allow imaging therethrough. In some embodiments, the outer shaft 322 can further include a preformed bend 329 therein to help orient or steer the device. A marker 315, such as a metal marker, can extend within the distal portion 313 to indicate the relative orientation of the catheter 300 when in use. For example, as shown in FIG. 4B, the innermost portion of the bend 329 can align with the marker 315.

Further, in some embodiments, the inner shaft 311 can move longitudinally within the hollow outer shaft 322 by sliding a ring on a handle (such as handle 200) connected to the catheter 300 to allow the inner shaft 311 to be exposed (as shown in FIGS. 4A-4B) or fully covered (as shown in FIGS. 5A-5C). In use, the inner shaft 311 can thus be extended out of the outer shaft to help drill through the occlusion and pulled in when dissection is not required (or when only blunt dissection is required). In some embodiments, the inner shaft 311 can be configured to be fixed at various points relative to the outer shaft 322 so as to vary the amount of exposed tip 103. Further, the shaft 311 can be fully removed from the outer shaft 322 to allow for placement of a guidewire therethrough.

Further, the device 300 can include an imaging element 399 similar to as described above with respect to device 100. The catheter 300 can be configured to image with the imaging element 399 both when the inner shaft 311 is extended distally out of the outer shaft 322 and when the inner shaft 311 is positioned within the outer shaft 322 (through the transparent distal portion 313).

The device 300 can further or alternatively include any of the features, materials, and/or dimensions described above with respect to device 100.

Referring to FIGS. 8A-10, in another embodiment, an exemplary catheter 800 can include both a separable inner shaft 811 and outer shaft 822 and an articulating feature 845 on the distal end of the outer shaft 822.

Figure 8A:
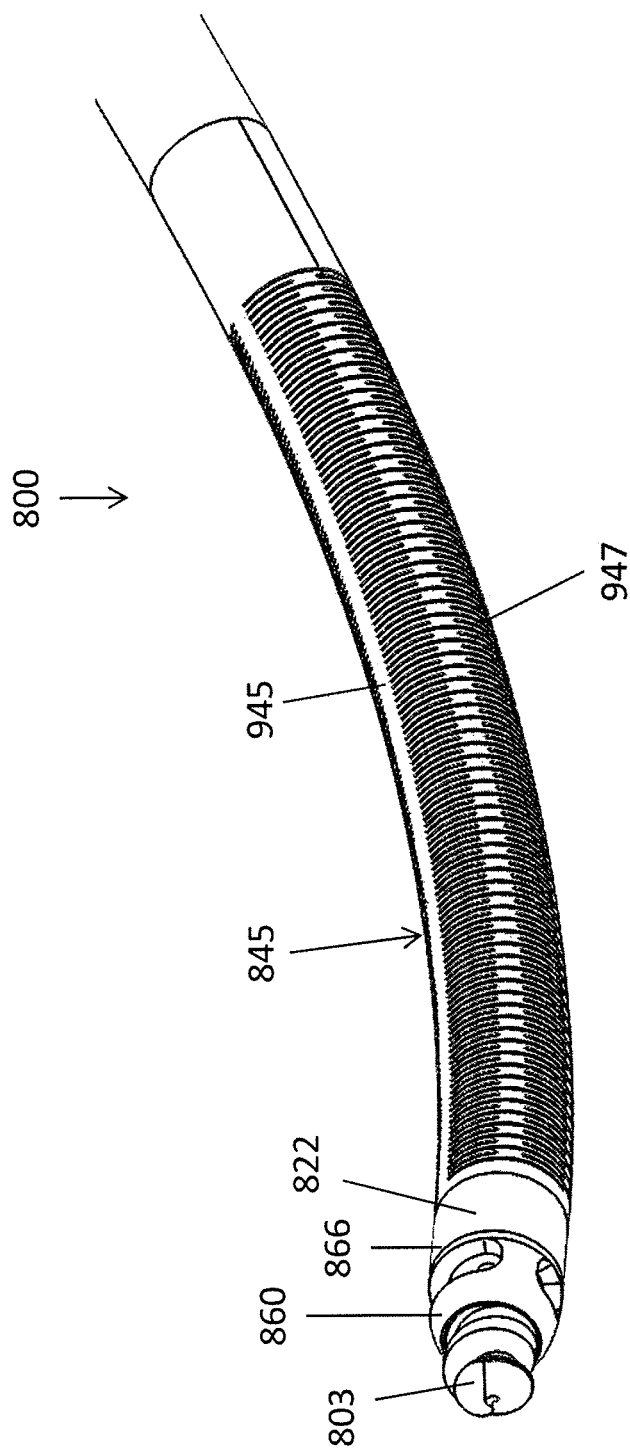
FIGS. 8A-8B show articulation of an occlusion crossing device having an articulating feature and separable inner and outer shafts.
Figure 8B:
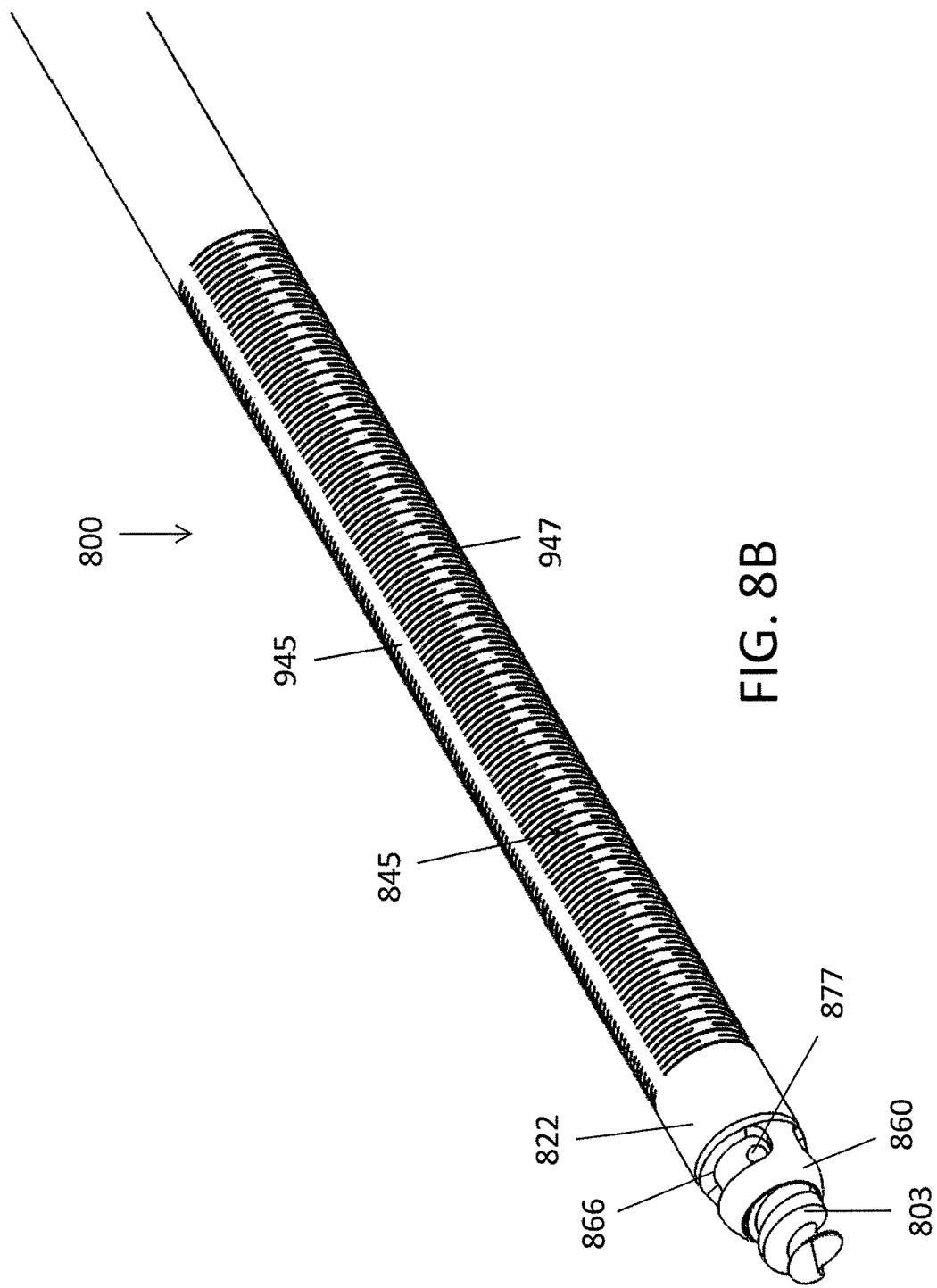
Figure 9A:
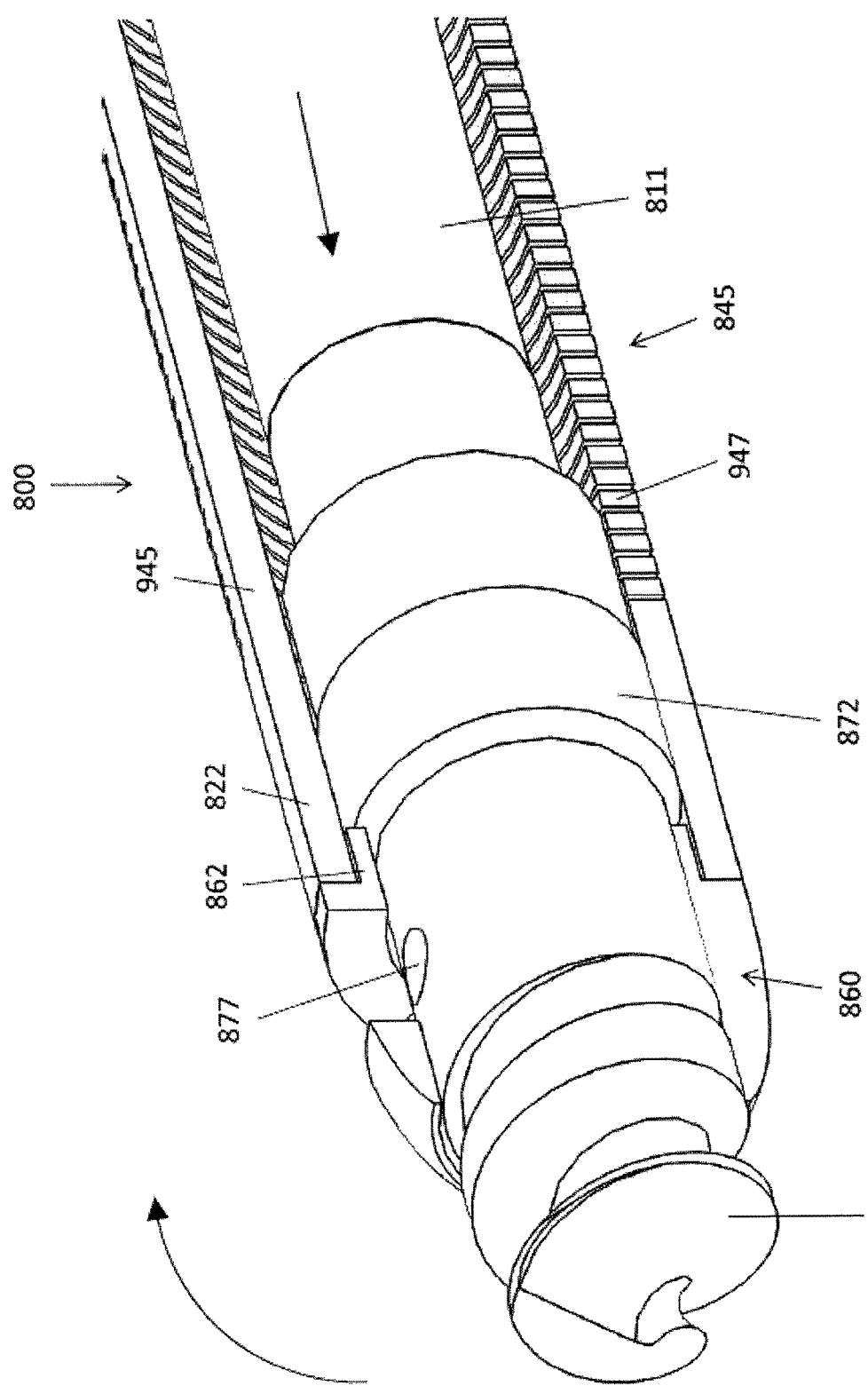

Referring to FIGS. 8A-8B, the articulating feature 845 can include a backbone 945 and a series of circumferential cuts 947. Further, as shown in FIG. 9A, a collar 860 attached to the outer shaft 822 can include an inner ledge 862 configured to extend radially inwards relative to the outer shaft 822. Likewise, the inner shaft 811 can include an annular member 872, such as a plastic bearing, that has a greater diameter than the rest of the inner shaft 811. Thus, when the inner shaft 811 is pushed distally, the annular member 872 of the inner shaft 811 can push against the inner ledge 862 of the collar 860. As a result, the outer shaft 822 can bend at the cuts 947 towards the backbone 945 (as shown by the arrows in FIG. 9A).

Figure 10:
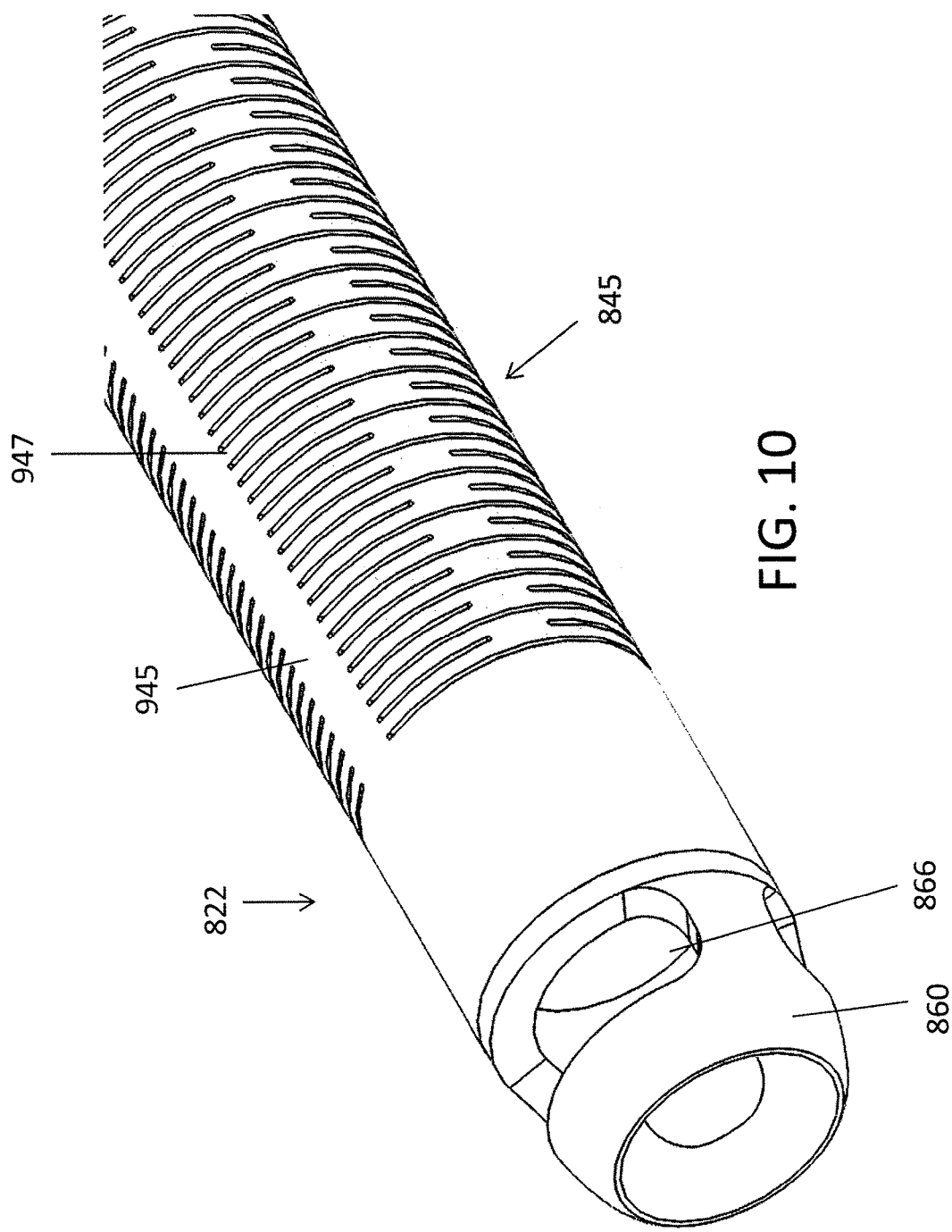
FIG. 10 shows the outer shaft of the occlusion crossing device of FIGS. 8A-8B with the inner shaft removed.

As shown in FIG. 10, the inner shaft 811 can be fully removable from the outer shaft 822 and collar 860 by pulling the inner shaft 811 proximally. By doing so, the outer shaft 822 can be used as a sheath, e.g., for guidewire placement.

Further, the inner shaft 811 can include an imaging element 877 element similar to as described above with respect to devices 100 and 300 that is rotatable with the inner shaft 811. The imaging element 877 can image through imaging windows 866 in the collar 860. Further, the inner ledge 862 can also function to properly align the imaging element 877 with the imaging windows 866 when the inner shaft 811 is within the outer shaft 822.

The inner shaft 811 can include a rotatable distal tip 803 similar to as described above with respect to devices 100 and 300. Likewise, the device 800 can alternatively or additionally include any of the materials and dimensions described above with respect to devices 100 and 300.

Figure 11A:
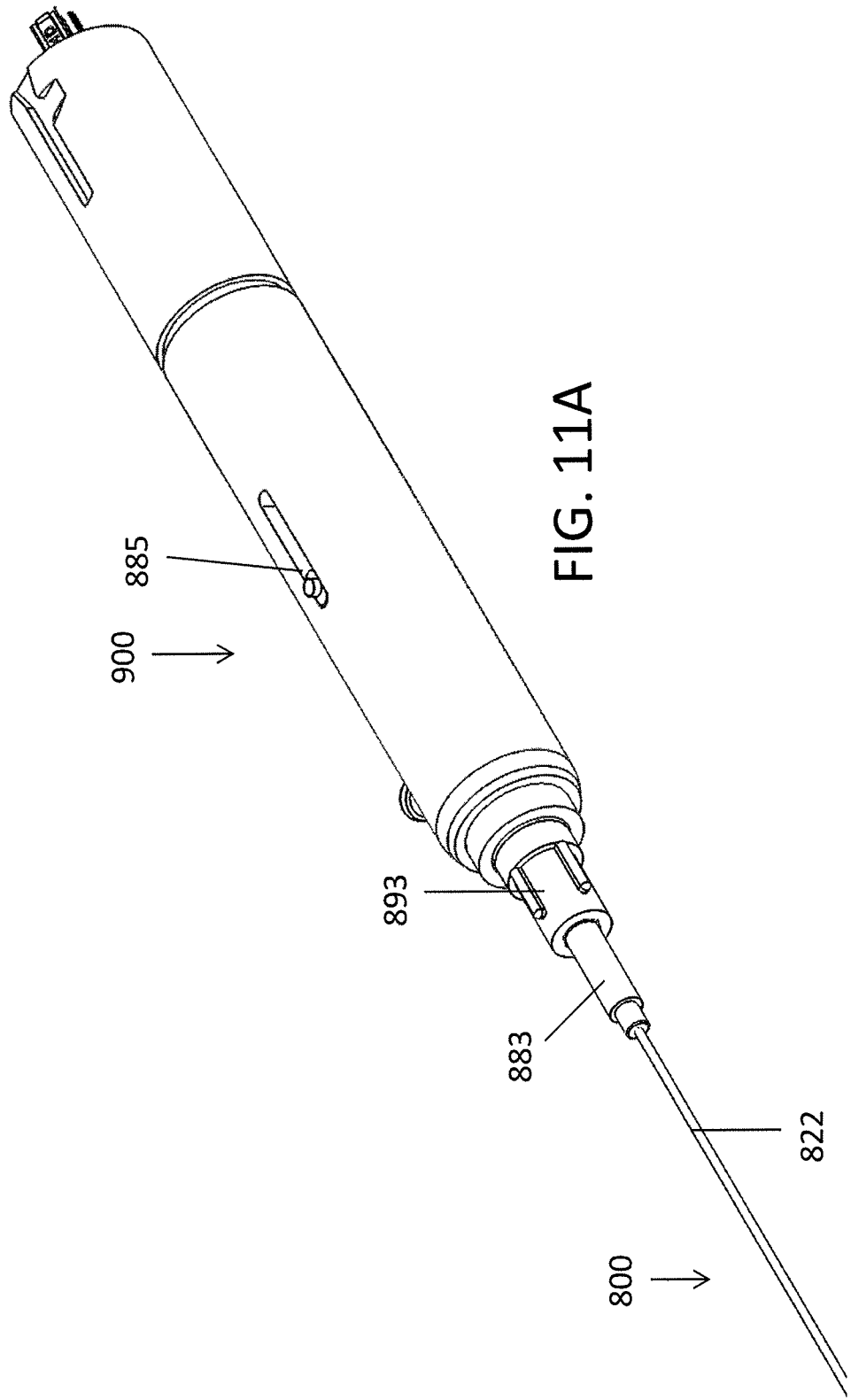

Referring to FIGS. 11A-11B, a handle 900 can be used to operate the device 800. The handle 900 can include a luer lock 883 configured to lock the inner shaft 811 and outer shaft 822 together longitudinally. The luer lock 883 can be configured to provide some relative longitudinal movement between the outer shaft 822 and the inner shaft 811 such that the inner shaft 811 can still move a small distance, such as between about 0.125 inches to 0.2 inches, to activate the articulating feature 845. For example, the inner shaft 811 can include an accordion or elastomeric segment to provide the additional relative movement. The actual displacement distance depends on the diameter of the outer shaft of the catheter, the degree of bending that is desired and the elongation/compression of the outer and inner shaft, respectively. The larger the diameter of the outer shaft, the greater the desired degree of bending, and the more compression/elongation of the shafts, the greater the required amount of displacement. Further, the luer lock 883 can be configured to allow the inner shaft 811 to rotate freely within the outer shaft so as to provide rotation of the sharp distal tip 803 connected to the inner shaft 811. The luer lock 883 can be configured such that the outer shaft can be rotated relative to the position of the handle. With the shaft in the articulated position, rotating the outer shaft will direct the catheter around or towards obstacles during use. If the luer lock 883 is disconnected, as shown in FIG. 11B, the inner shaft 811 can be pulled out of the outer shaft 822 by the handle, leaving the outer shaft 822 in place, such as for guidewire placement.

The handle 900 can further include a lever 885 or ring configured to control the axial movement of the inner shaft 811 (and thus the articulation of the device 800). In some embodiments, the lever 885 can include a locking mechanism that allows the device 800 to stay bent at a set angle. The handle 900 can also include a rotation element 893 attached to the outer shaft 822 and configured to rotate the outer shaft 822, such as 360 degrees, to position the bend of the device 800 in the desired orientation.

Figure 12:
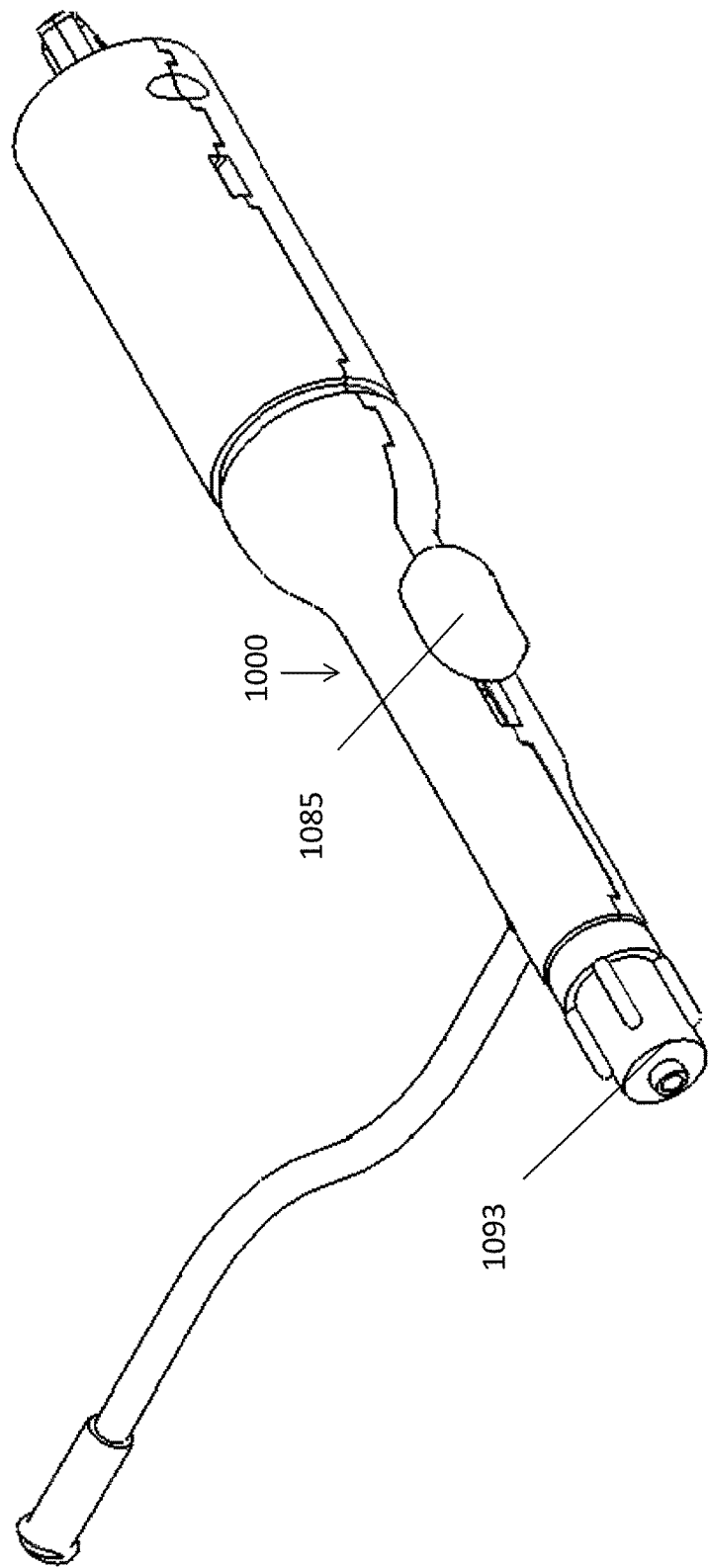
FIGS. 12 and 13 show another exemplary handle for use with the occlusion crossing device of FIGS. 8A-8B.
Figure 13:
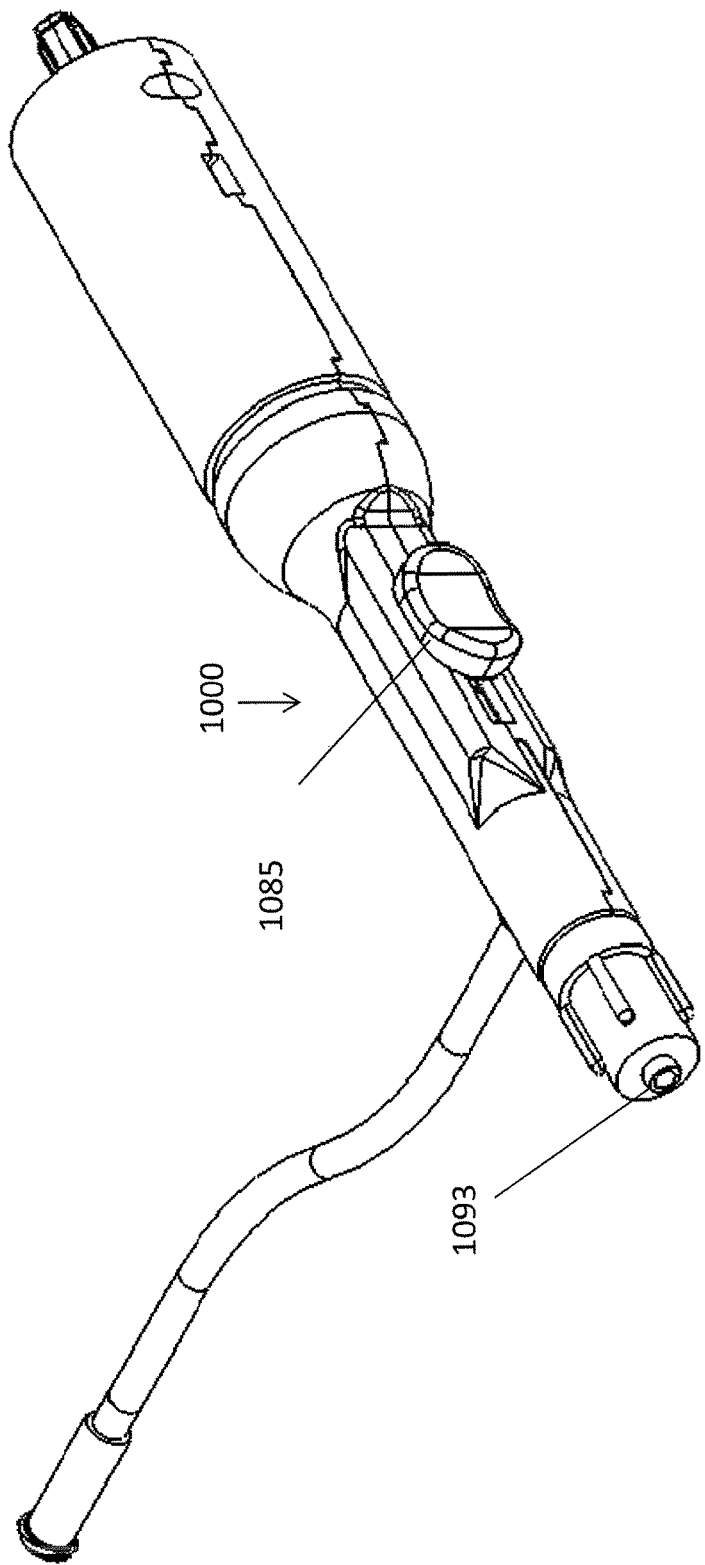

Another exemplary handle 1000 is shown in FIGS. 12-13. The handle 1000 can include many of the features of handle 900. A slide button 1085 can be used to control the axial movement of the inner shaft. The rotation element 1093 can be configured to rotate the outer shaft 822.

Furthermore, in some embodiments, the connection between the outer and inner shafts within the handle can be configured such that the two shaft snap together, axially fixing the proximal ends together, but allowing them to rotate independently. In other embodiments, a third element could be used to key, link, or peg the two shafts together.

Features of the handles 900, 1000, though described for use with catheter 800, can likewise be used with catheters 100, 300.

The distal end of another embodiment of a catheter 1400 is shown in FIGS. 14A-14B. The catheter 1400 is similar to catheters 100, 300, 800 except that it includes a smooth distal tip 103 and a molded distal portion 1410. Thus, the distal tip 103 can have a smooth angled surface 1413 that is non-fluted and comes together in a slightly convex distal point 1415 (i.e., the tip can be frusto-conical). The distal tip 103 of FIGS. 14A, 14B can advantageously provide less aggressive drilling through the occlusion. The distal tip 103 of FIGS. 14A and 14B can be used in place of any of the distal tips described with respect to catheters 100, 300, 800. Likewise, the catheter 1400 can include a molded distal portion 1422. The molded distal portion 1422 can be similar to the distal end of the catheter 300 and can include a bushing 1424, a transparent section 1422, and the scaffolding 1452 of the outer shaft. Further, an imaging fiber 1499 can run down the central axis of the device, as described above with respect to other embodiments. Any of the features of catheter 100, 300, 800 can be used in addition to, or as an alternative to, the features described with respect to catheter 1400. Likewise, the catheter 1400 can be used with a handle having some or all of the features of handles 200, 900, or 1000.

In some embodiments, all or a portion of the outer shaft of the catheters described herein can be clear to allow imaging therethrough. Further, in some embodiments, the catheters described herein can include a balloon to occlude for better imaging. The balloon can be a clear balloon to allow imaging therethrough.

As described above, the catheters 100, 300, 800, 1400 can include an imaging element. The imaging element can include an optical fiber, such as an optical coherence tomography (OCT) imaging fiber. The optical fiber can extend within the driveshaft or inner shaft so as to extend substantially along the central axis of the catheter for the entire length of the fiber. The fiber can be attached at the distal end of the driveshaft or inner shaft and/or the distal tip, but can be otherwise free to float within the driveshaft. The imaging fiber can transfer an OCT signal for imaging of the vessel in which the device is placed. In some embodiments, the imaging fiber can have a polyimide coating therearound within the length of the driveshaft to support and protect the fiber as it spins within the driveshaft. Further, the handles described herein can be configured to accommodate a certain amount of slack in the fiber to facilitate extension and retraction of drive shaft against hollow shaft.

The imaging element can further include a mirror oriented at an angle (such as a 30-60 degree angle, e.g., 45 degrees) with respect to the central axis of the fiber such that light coming out of the fiber will bounce off the mirror and into the adjacent tissue. Glue can be used to hold the distal end of the optical fiber in place. The glue can have a refractive index configured to be appropriately mismatched with the refractive index of the fiber, as described in U.S. patent application Ser. No. 12/790,703, titled "OPTICAL COHERENCE TOMOGRAPHY FOR BIOLOGICAL IMAGING," filed May 28, 2010, Publication No. US-2010-0305452-A1; and International Patent Application No. PCT/US2013/031951, titled "OPTICAL COHERENCE TOMOGRAPHY WITH GRADED INDEX FIBER FOR BIOLOGICAL IMAGING," filed Mar. 15, 2013, both of which are incorporated by reference in their entireties. Further, the glue can have a meniscus shape along its outer edge, as described in International Patent Application No. PCT/US2013/031951 titled "OPTICAL COHERENCE TOMOGRAPHY WITH GRADED INDEX FIBER FOR BIOLOGICAL IMAGING," filed Mar. 15, 2013, incorporated by reference herein. The meniscus shape can advantageously ensure that the light reflected back from the surface of the glue and back into the fiber is significantly less than the light referenced.

The driveshaft or inner shaft, and thus the imaging element or optical fiber, can be configured to rotate continuously at high speeds, such as greater than 500 rpm, greater than 600 rpm, greater than 700 rpm, greater than 800 rpm, greater than 900 rpm, or greater than 1,000 rpm, e.g., between 500-1,000 rpm, in one or both directions to provide OCT imaging around the inner circumference of the vessel. Such high speed rotation in a single direction or in different directions as chosen by the user (as opposed to requiring rotation alternately in both directions to manage the optical fiber) allows for the gathering of image data more quickly, thereby providing more accurate and up-to-date images during use of the device 100. For example, images can be generated at a rate of greater than 6 frames per section (fps), such as greater than or equal to 8 fps or greater than or equal to 10 fps, such as approximately 16.67 fps. In an exemplary embodiment, the rate of Laser sweep, such as approximately 20 KHz, can be configured to keep up with at 16.67 frames per second with about 1200 lines per frame.

Advantageously, because the optical fiber runs through the center of the catheters described herein, the catheters can be small in diameter. For example, the outer diameter of the catheters described herein can be less than 0.10", such as less than 0.08", such as less than 0.07", less than 0.06", or less than 0.05". Accordingly, the catheters described herein can advantageously be used in small-diameter peripheral arteries and coronary arteries.

In some embodiments, the catheters described herein can be configured to be attached to a drive system. The drive system can include a rotary optical junction configured to rotate the fiber. Exemplary drive systems that could be used in conjunction with the devices herein are described in U.S. patent application Ser. No. 13/654,357, titled "ATHERECTOMY CATHETERS AND NON-CONTACT ACTUATION MECHANISM FOR CATHETERS," filed Oct. 17, 2012 and International Patent Application No. PCT/US2013/032089, titled "ATHERECTOMY CATHETER DRIVE ASSEMBLIES," filed Mar. 15, 2013, each incorporated herein by reference in its entirety.

Figure 6A:
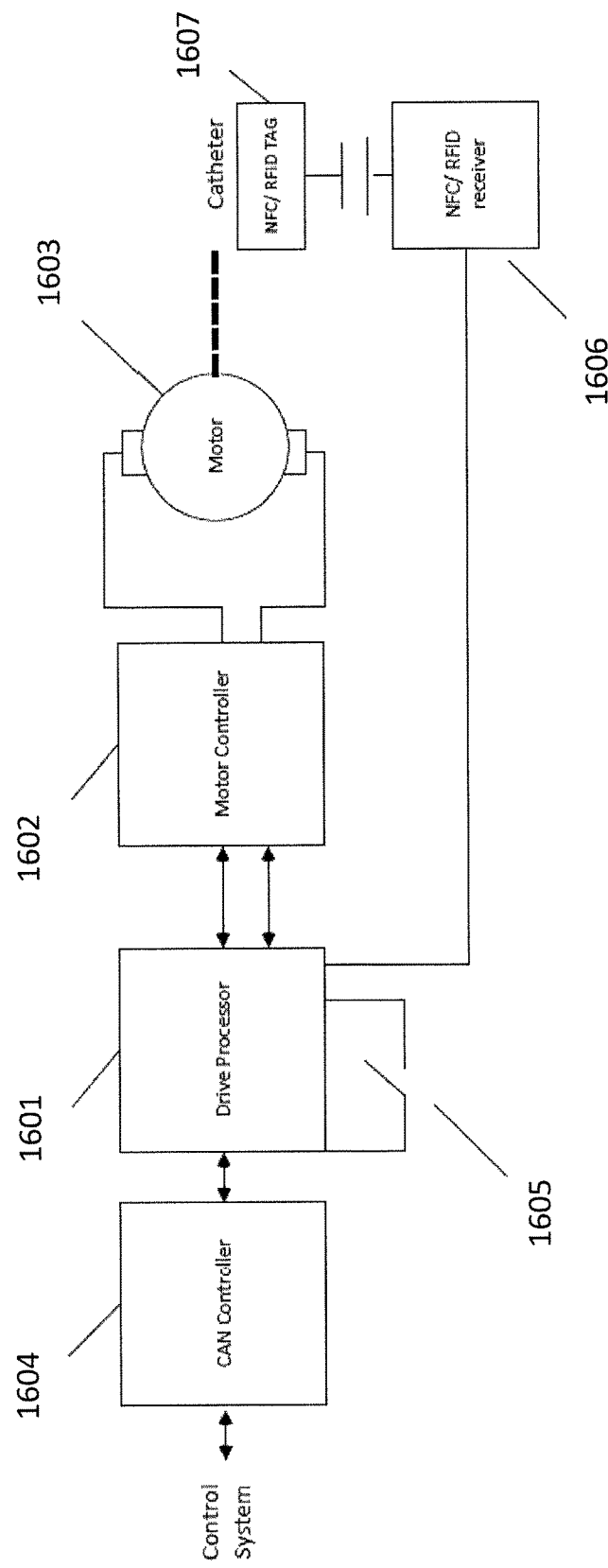
FIGS. 6A and 6B are exemplary block diagrams of drive systems for the catheters described herein.

In some embodiments, the drive system can communicate with the control system via a communication bus, which in some embodiments can be a CAN bus 2.0B. This communication can be employed to convey status to the control system or console, such as direction, speed, run status, and other information. It can also be employed to send control information to the drive system, such as run command, speed, direction, and setting of parameters for compensations of mechanical characteristics of the catheters. Referring to FIG. 6A, in one embodiment, a drive processor 1601 is used as the main controlling element for the drive system. The drive processor 1601 controls the motor 1603 through a motor controller 1602, which receives commands and returns status from/to the drive processor 1601. The drive processor 1601 can, in addition to simple speed and direction control, also implement algorithms to optimize catheter performance. The drive processor 1601 communicates with the control system (e.g., the console for the device) via the CAN controller 1604 to send and receive commands and status. In addition, in this embodiment a switch 1605 on the drive processor 1601 housing allows local control of the run state. The switch 1605 can be replaced with alternative hardware inputs, such as buttons, toggles, or knobs.

Figure 6B:
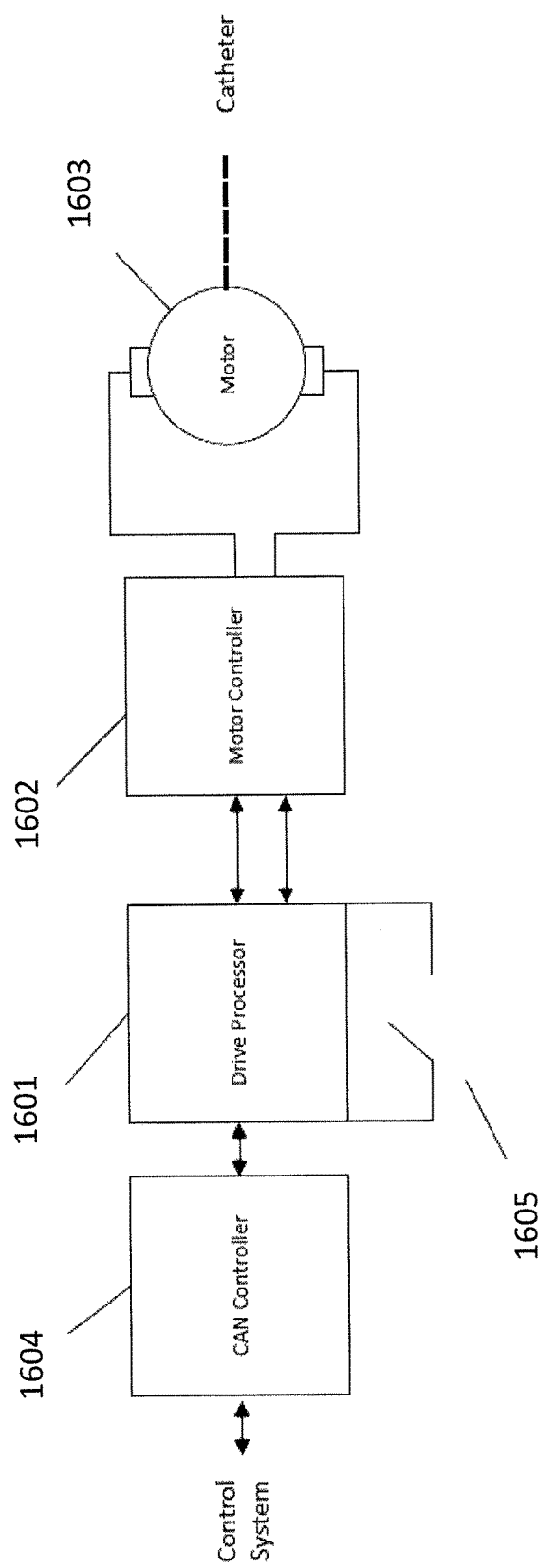

Further, in some embodiments the drive system can communicate with the catheter via NFC or RFID to obtain information about the catheter. As an example, this information can include catheter type, optimal rotational speed and direction, serial number, amongst many possible parameters. Referring to FIG. 6B, the drive system communicates with the catheter via a NFC/RFID reader 1606 and a NFC/RFID tag 1607 in the catheter to obtain information stored in the tag.

The drive system can be configured to allow the driveshaft and cutter to rotate continuously in the clockwise or the counterclockwise direction depending upon user preference. Therefore, in some embodiments, the drive system can include a user-addressable switch, such as a toggle, to set the desired direction.

Further, in some embodiments, the drive system can include a mechanism to determine the amount of rotation of the driveshaft in the clockwise or counterclockwise directions. Referring to FIGS. 6A and 6B, in one embodiment, for example, the drive system can provide information related to the direction of the motor. Speed and direction can be sensed by the control system (or console) by a data line in the umbilical, which can be a dedicated line or a multiplexed signal. The dedicated line can carry an analog or a digital signal. In one embodiment, a dedicated voltage line carries six discrete velocities (vector speed+direction) that are interpreted by the control system or console in order to infer speed and direction of the catheter.

Figure 7B:
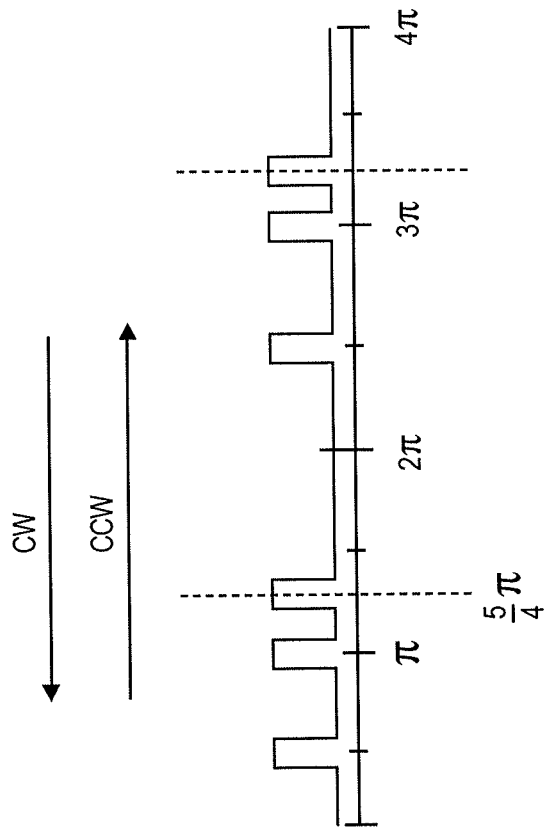
FIGS. 7A-7B show an exemplary method for detecting the position of the driveshaft of a catheter.
Figure 7A:
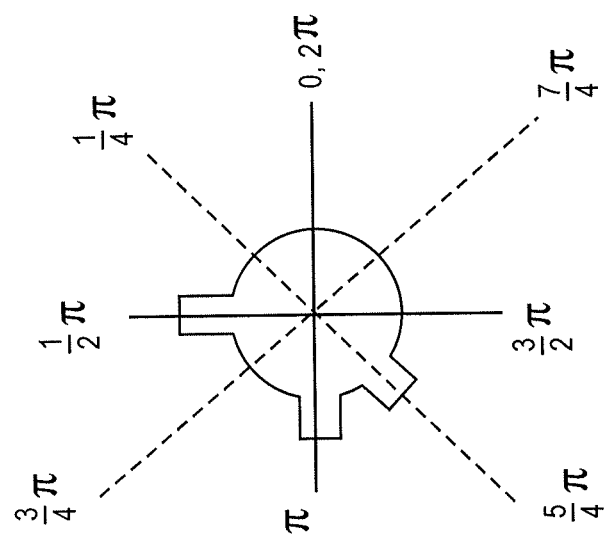

Referring to FIGS. 7A-7B, in on embodiment, a flag in the drive system can include either an asymmetric design or an asymmetric positioning of the flags around the motor (see FIG. 7A). A controller can then sense motor direction by detecting the distinct series of flag spacing and/or width, as shown in FIG. 7B.

Further, in some embodiments, the drive system can be configured to rotate the driveshaft at several discrete rates and/or include a knob to allow for user-chosen continuously variable speeds.

Any of the catheters described herein can be shape-set or include shape-set features to enhance trackability and navigability.

As used herein, an imaging element can include the OCT optical fiber, such as the distal end of the optical fiber, as well as the mirror and adhesive used to hold the mirror and optical fiber in place.

As described above, the catheters described herein can include optical coherence tomography imaging, such as common path OCT. Such OCT systems are described in U.S. patent application Ser. No. 12/829,267, titled "CATHETER-BASED OFF-AXIS OPTICAL COHERENCE TOMOGRAPHY IMAGING SYSTEM," filed Jul. 1, 2010, Publication No. US-2010-0021926-A1; U.S. patent application Ser. No. 12/790,703, titled "OPTICAL COHERENCE TOMOGRAPHY FOR BIOLOGICAL IMAGING," filed May 28, 2010, Publication No. US-2010-0305452-A1; and International Patent Application PCT/US2013/031951 titled "OPTICAL COHERENCE TOMOGRAPHY WITH GRADED INDEX FIBER FOR BIOLOGICAL IMAGING," filed Mar. 15, 2013, all of which are incorporated by reference in their entireties. Alternatively, other types of imaging could be used with the catheters described herein. For example, the devices described herein could be configured to work with infrared spectroscopy or ultrasound.

The catheters 100, 300, 800, 1400 described herein can be used for occlusion-crossing within blood vessels. Advantageously, the devices can advantageously provide increased trackability through bending/steering and high imaging speed during such crossing.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. An occlusion crossing device comprising:
   an outer shaft;
   an inner shaft extending within the outer shaft, the inner shaft including a drill tip at a distal end thereof;
   an optical fiber extending within the inner shaft substantially along a central axis of the inner shaft, a distal tip of the optical fiber attached to the drill tip; and
   a handle attached to the inner shaft and the outer shaft and configured rotate the inner shaft and drill tip at speeds of greater than 500 rotations per minute,
   wherein the inner shaft is removably coupled with the outer shaft such that the inner shaft moves longitudinally with respect to the outer shaft when a force is applied to the inner shaft in a longitudinal direction to allow the outer shaft to bend with respect to the central axis while coupled to the inner shaft.

2. The occlusion crossing device of claim 1, wherein the force is a pushing force applied in a distal direction or a pulling force applied in a proximal direction.

3. The occlusion crossing device of claim 1, wherein the inner shaft is removably coupled with the outer shaft with a lock configured to lock and unlock the inner shaft relative to the outer shaft, wherein the lock is configured to provide relative longitudinal movement of outer shaft relative to the inner shaft during bending of the outer shaft with respect to the central axis.

4. The occlusion crossing device of claim 1, wherein the outer shaft includes an articulating feature configured to allow the outer shaft to bend, the articulating feature activated by moving the inner shaft along the central axis relative to the outer shaft.

5. The occlusion crossing device of claim 4, wherein the articulating feature includes a backbone and a plurality of circumferential cuts.

6. The occlusion crossing device of claim 4, wherein the inner shaft includes an annular member configured to engage with an inner lip of the outer shaft to bend the outer shaft when the inner shaft is pushed distally.

7. The occlusion crossing device of claim 4, wherein the inner shaft includes an annular member configured to engage with an inner lip of the outer shaft to bend the outer shaft when the inner shaft is pulled proximally.

8. The occlusion crossing device of claim 1, wherein the outer shaft includes a preformed bend therein.

9. The occlusion crossing device of claim 1, wherein the outer shaft further comprises a marker positioned with respect to the preformed bend such that an orientation of the outer shaft can be determined during imaging.

10. The occlusion crossing device of claim 1, wherein the outer shaft includes a transparent distal portion configured to allow imaging with the optical fiber therethrough.

11. The occlusion crossing device of claim 1, wherein the handle is configured to rotate the inner shaft and drill tip at speeds of greater than 1,000 rotations per minute.

12. The occlusion crossing device of claim 1, wherein the handle is configured to rate the inner shaft and drill tip at speeds of greater than 500 rotations per minute such that images can be generated from the optical fiber at a rate of greater than or equal to 8 frames per second.

13. The occlusion crossing device of claim 1, wherein the optical fiber is a common path optical coherence tomography fiber.

14. The occlusion crossing device of claim 1, wherein the drill tip includes a plurality of spiral cutting edges.

15. The occlusion crossing device of claim 1, wherein the drill tip is a substantially smooth frusto-conical tip.

16. The occlusion crossing device of claim 1, further comprising a monorail guidewire lumen extending along the outer shaft.

17. The imaging occlusion crossing device of claim 1, wherein an outer diameter of the outer shaft is less than 0.08 inches.

18. The occlusion crossing device of claim 1, wherein the inner shaft is configured to be removed from the outer shaft while at least a portion of the outer shaft is in place within a vessel.

19. The occlusion crossing device of claim 1, wherein the inner and outer shafts are axially movable with respect to each other at a proximal region of the device and axially fixed at a distal region of the device when the force is applied to the inner shaft.

20. The occlusion crossing device of claim 1, wherein the inner shaft is configured to rotate with respect to the outer shaft during bending of the outer shaft with respect to the central axis.

21. The occlusion crossing device of claim 1, wherein the inner shaft is configured to be fixed at various points relative to the outer shaft so as to vary an amount that the drill tip is exposed.

22. A method of crossing an occlusion, comprising:
inserting a device into a vessel having an occlusion therein, the device having an inner shaft having an optical fiber coupled thereto and removably coupled to an outer shaft;
causing a distal end of the device to bend with respect to a central axis of the device by applying a force to the inner shaft in a longitudinal direction while the inner shaft is coupled with the outer shaft;
rotating the inner shaft relative to the outer shaft such that a drill tip on the inner shaft drills through the occlusion; and
generating images with the optical fiber at a rate of greater than or equal to 8 frames per second while rotating the inner shaft.

23. The method of claim 22, further comprising:
removing the inner shaft from the outer shaft while at least a portion of the outer shaft is in place within the vessel; and
inserting a guidewire through the outer shaft.

24. The method of claim 22, wherein causing the distal end of the device to bend comprises causing the inner shaft to displace longitudinally with respect to the outer shaft while the inner shaft is coupled with the outer shaft.

25. The method of claim 24, wherein the inner shaft is displaced longitudinally by a distance of between about 0.125 inches to about 0.2 inches with respect to the outer shaft.

26. The method of claim 22, wherein bending the distal end comprises pushing or pulling on the inner shaft.

27. The method of claim 26, further comprising using a marker on the device to orient the bent distal end of the device.

28. The method of claim 22, wherein rotating the inner shaft comprises rotating at more than 500 rotations per minute.

29. The method of claim 22, wherein rotating the inner shaft comprises rotating the inner shaft while coupled to the outer shaft.

30. The method of claim 22, wherein rotating the inner shaft comprises rotating the inner shaft while causing the distal end of the device to bend.

31. The method of claim 22, wherein the images are generated while the device is bending.

* * * * *